(12) United States Patent
Gordon et al.

(10) Patent No.: US 6,684,104 B2
(45) Date of Patent: Jan. 27, 2004

(54) GASTRIC STIMULATOR APPARATUS AND METHOD FOR INSTALLING

(75) Inventors: Pat L. Gordon, Wayzata, MN (US); David A. Jenkins, Flanders, NJ (US)

(73) Assignee: Transneuronix, Inc., Mt. Arlington, NJ (US)

( * ) Notice: Subject to any disclaimer, the term of this patent is extended or adjusted under 35 U.S.C. 154(b) by 0 days.

(21) Appl. No.: 10/189,120

(22) Filed: Jul. 2, 2002

(65) Prior Publication Data

US 2003/0055463 A1 Mar. 20, 2003

Related U.S. Application Data

(63) Continuation-in-part of application No. 09/466,731, filed on Dec. 17, 1999, now Pat. No. 6,542,776.
(60) Provisional application No. 60/129,198, filed on Apr. 14, 1999, provisional application No. 60/129,199, filed on Apr. 14, 1999, and provisional application No. 60/129,209, filed on Apr. 14, 1999.

(51) Int. Cl.[7] ............................................... A61N 1/36
(52) U.S. Cl. ........................................................ 607/40
(58) Field of Search .............................. 607/40, 39, 41, 607/48, 50, 68, 72, 73, 116, 133, 148, 149

(56) References Cited

U.S. PATENT DOCUMENTS

| | | |
|---|---|---|
| 3,646,940 A | 3/1972 | Timm et al. |
| 5,365,926 A | 11/1994 | Desai |
| 5,423,872 A | 6/1995 | Cigaina |
| 5,620,481 A | 4/1997 | Desai et al. |
| 5,630,426 A | 5/1997 | Eggers et al. |
| 5,690,691 A * | 11/1997 | Chen et al. .................... 607/40 |
| 5,716,392 A | 2/1998 | Bourgeois et al. |
| 5,873,849 A | 2/1999 | Bernard |
| 6,029,091 A | 2/2000 | de la Rama et al. |
| 6,041,258 A | 3/2000 | Cigaina et al. |
| 6,085,119 A | 7/2000 | Scheiner et al. |
| 6,146,391 A | 11/2000 | Cigaina |
| 6,165,180 A | 12/2000 | Cigaina et al. |
| 6,205,361 B1 | 3/2001 | Kuzma et al. |
| 6,321,124 B1 | 11/2001 | Cigaina |
| 6,381,495 B1 | 4/2002 | Jenkins |
| 6,402,744 B2 | 6/2002 | Edwards et al. |
| 6,449,511 B1 * | 9/2002 | Mintchev et al. ............. 607/40 |

* cited by examiner

*Primary Examiner*—Kennedy Schaetzle
(74) *Attorney, Agent, or Firm*—Fitch, Even, Tabin & Flannery

(57) ABSTRACT

Apparatus for stimulating neuromuscular tissue of the gastrointestinal tract and methods for installing the apparatus to the neuromuscular tissue. The pulse generator is provided with a switching matrix, and may stimulate the tissue in a time-varying manner by selecting pairs of electrodes and altering the polarities thereof while stimulating the tissue. In addition, a real-time clock allowing a trigger for on and off modes, the time clock could also allow for a trigger to change parameters. Such parameters that could be changed are pulse width, amplitude, duty cycle (amount of time of pulse and time between pulses, or series of pulses), frequency, polarity, choice of unipolar versus bi-polar, and electrode on-off. The electrical stimulation utilizes a plurality of electrodes connected to at least one organ in the gastrointestinal tract of a patient along a peristaltic flow path with each of the electrodes being connected at a different location along the peristaltic flow path. Electrical pulses are provided to the organ from a first set of the plurality of electrodes and second electrical pulses are provided to the organ from a second set of electrodes. The electrical pulses provided are in an independent non-phased relationship for maintaining therapeutic regulation of peristaltic flow through the at least one organ in the gastrointestinal tract while defeating the body's natural tendency for adaption.

31 Claims, 13 Drawing Sheets

```
┌─────────────────────────────────────────────────┐
│ 112                  114                        │
│ DAY 1                        26 JUNE 1999       │
│         118                                     │
│ CYCLE 1   120   START TIME =    12:00 A         │
│           122   STOP TIME =     6:50 A          │
│           124   PULSEWIDTH =    500 µSEC        │
│           126   PULSE INTERVAL= 25 mSEC         │
│           128   ON-TIME =       2 SEC           │
│           130   OFF-TIME =      3 SEC           │
│                 PULSE HEIGHT=   1V              │
│                                                 │
│                 ELECTRODE A = +  — 132          │
│                 ELECTRODE B = 0  — 134          │
│                 ELECTRODE C = 0  — 136          │
│                 ELECTRODE D = -  — 138          │
│                                                 │
│ CYCLE 2         START TIME=     6:51 A          │
│                 STOP TIME=      11:00 A         │
│                 PULSE WIDTH=    100 µSEC        │
│                 PULSE INTERVAL= 20 mSEC         │
│                 ON-TIME =       2 SEC           │
│                 OFF-TIME=       3 SEC           │
│                 PULSE HEIGHT =  0.5V            │
│                 ELECTRODE A= 0                  │
│                 ELECTRODE B= +                  │
│                 ELECTRODE C= -                  │
│                 ELECTRODE D= 0                  │
└─────────────────────────────────────────────────┘
```

116

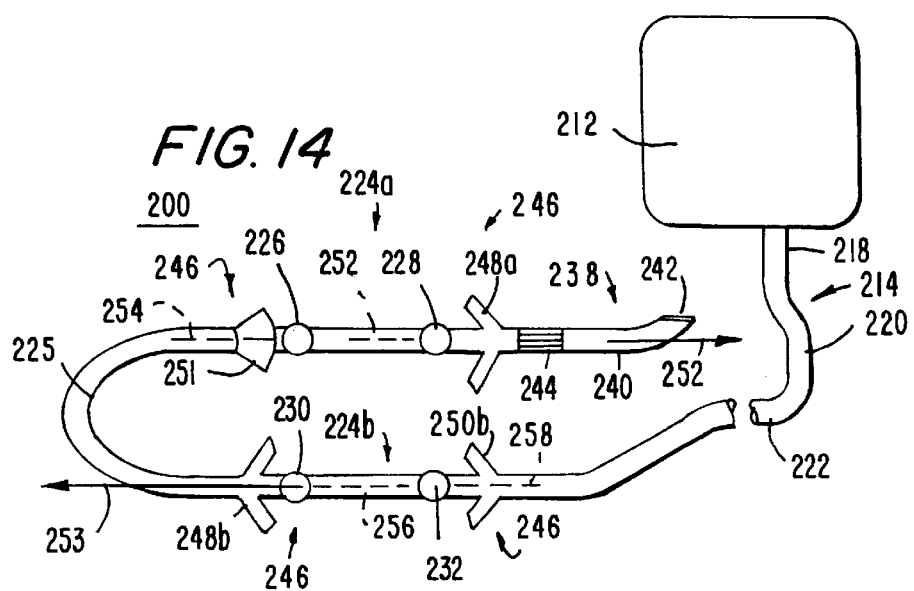
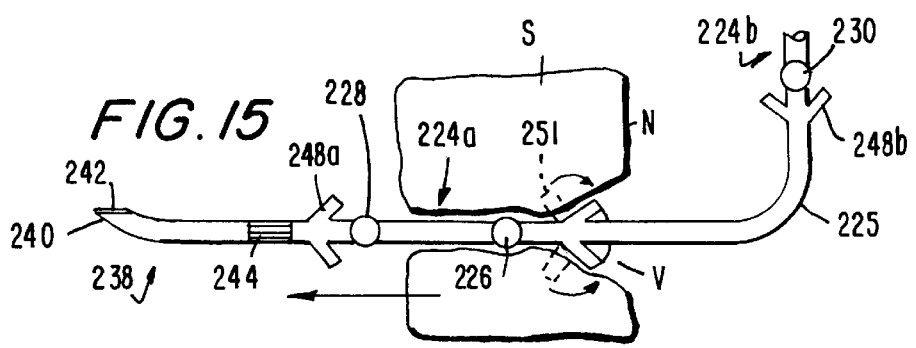
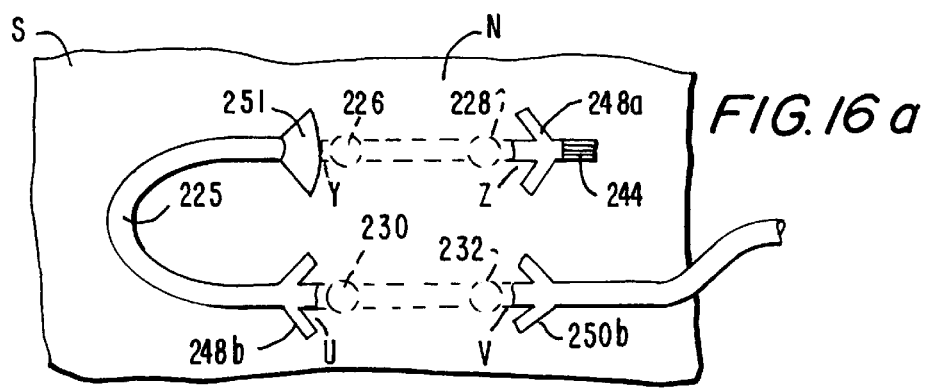
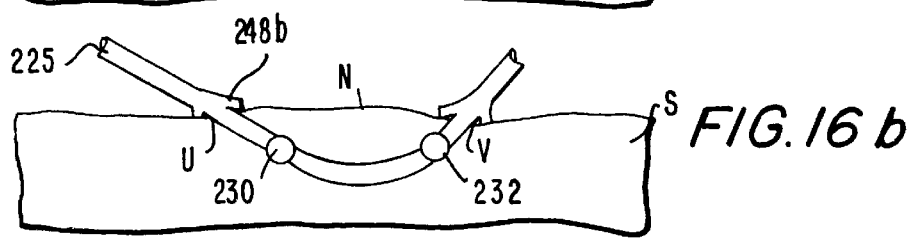

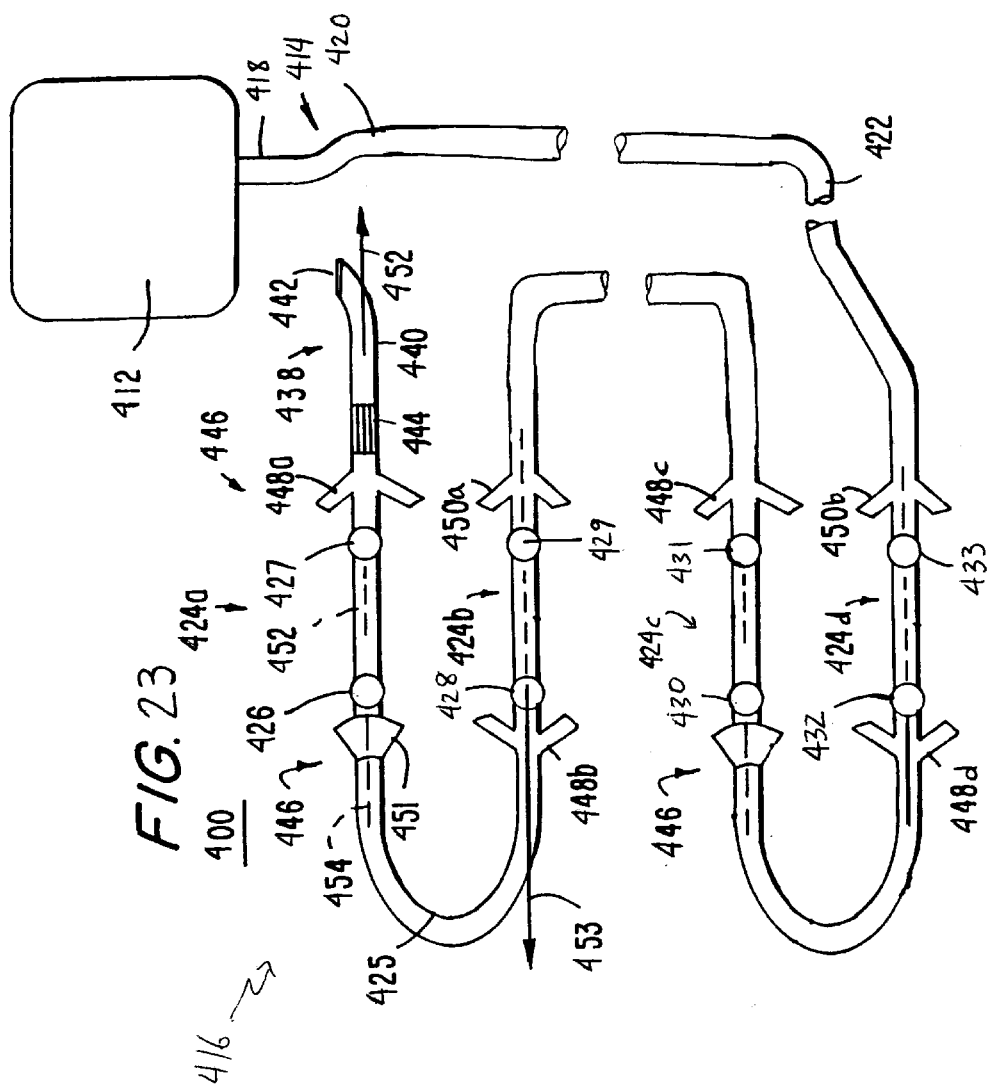

GASTRIC STIMULATOR APPARATUS AND METHOD FOR INSTALLING

This is a continuation-in-part of prior application Ser. No. 09/466,731, filed Dec. 17, 1999, now U.S. Pat. No. 6,542,776 which application claims the benefit of U.S. Provisional Application No. 60/129,198, U.S. Provisional Application No. 60/129,199, and U.S. Provisional Application No. 60/129,209, all of which were filed Apr. 14, 1999, each of which is incorporated by reference in its entirety herein.

BACKGROUND OF THE INVENTION

This invention relates to electrical stimulation apparatus and methods for use in stimulating body organs, and more particularly to implantable apparatus for stimulating neuromuscular tissue of the viscera of the organ structure, including the gastrointestinal tract and methods for installing the apparatus in a patient.

The field of electrical tissue stimulation has recently been expanded to include devices which electrically stimulate the stomach or intestinal tract with electrodes implanted in the tissue. These gastric stimulators have been found to successfully combat obesity in certain studies. Medical understanding as to how this treatment functions to reduce obesity is currently incomplete. However, patients successfully treated report achieving normal cycles of hunger and satiation.

An apparatus and treatment method for implementing this therapy was described in U.S. Pat. No. 5,423,872 to Dr. Valerio Cigaina, which is hereby incorporated by reference in its entirety herein. The apparatus described in the Cigaina patent stimulates the stomach antrum pyloricum with trains of stimulating pulses during an interval of about two seconds followed by an "off" interval of about three seconds.

U.S. Pat. No. 5,836,994 to Bourgeois describes a laparoscopic device which has a needle which passes through the tissue being stimulated, and a thread attached at one end to the needle and at the other end to an implantable pulse generator (IPG) lead. The entire device can be inserted into the body via a laparoscopic type tube, or trocar, as it is relatively long and narrow. Many devices are known to be inserted through a trocar by having a needle attached with a thread to the devices.

Copending Cigaina U.S. Application PCT/US98/1042, filed on May 21, 1998, and copending Cigaina U.S. application Ser. No. 09/122,832, filed Jul. 27, 1998, now U.S. Pat. No. 6,041,258 both of which are incorporated by reference in their entirety herein, describe a novel apparatus wherein the needle is incorporated into the end of the lead. Once the electrodes are inserted into the viscera, the electrodes are fixed in place by partially opposing tines.

The above apparatus and methods of installation generally incorporate a pair of electrodes for stimulating the tissue. As illustrated in FIG. 1, a first electrode 1 and a second electrode 2 are implanted in the patient's tissue 3. When electrical stimulation is applied to the tissue 3, a pulsed electric field 4 propagates outward from the electrodes 1 and 2 in a direction 5 generally perpendicular to the direction 6 of electrode axis, typical of a directional dipole.

Under certain circumstances, it may be necessary to provide electrical pulses that stimulate a greater area of tissue in order to obtain the desired tissue response and entrainment. For example, certain patients may benefit from stimulation over a larger area of tissue. Thus, there is a need to provide an electrode apparatus that stimulates tissue over a greater area in a more uniform or omnidirectional fashion.

Moreover, variations in the stimulation location, direction, duration, and intensity over time may be beneficial. It is an advantage of the invention to provide an apparatus and methods of stimulation wherein the stimulation patterns may be varied over time.

It is also an advantage of the invention to provide an apparatus and methods of stimulation wherein the electrodes may be implanted in a minimally invasive manner, such as laparoscopically, which allows substantially equidistant spacing of the electrodes.

SUMMARY OF THE INVENTION

These and other objects of the invention are accomplished in accordance with the principles of the invention by providing apparatus and methods for attaching such apparatus to neuromuscular tissue of the viscera, and particularly, the gastrointestinal tract. The apparatus includes at least four closely spaced stimulating electrodes electrically connected to a pulse generator that supplies electrical stimulating pulses to the neuromuscular tissue. According to a preferred embodiment, an electrode assembly includes a first electrode-pair attachment member supporting a first pair of electrodes and a second electrode-pair attachment member supporting a second pair of electrodes. Each electrode-pair attachment member includes first and second anchor members that secure the electrode attachment member and the electrodes in the tissue. Such anchor members may be a set of resilient tines which abut the tissue and prevent relative movement with respect thereto.

In the most preferred embodiment, the electrode assembly has a pair of electrode-pair attachment members arranged in parallel, each having a respective penetrative mechanism and a severable connecting member for removably attaching the penetration mechanism to the electrode attachment member. The first electrode-pair attachment member pierces the tissue with the first penetrative mechanism and anchors itself at a first location. The second electrode-pair attachment member pierces the tissue with the second penetrative mechanism and anchors itself at a second location, and in a position substantially parallel to the first electrode-pair attachment member.

In another preferred embodiment, the electrode assembly has the two of electrode-pair attachment members arranged in series. One penetration mechanism is provided and connected to the one of the first and second electrode-pair attachment members, and a bridging portion connects the first and second electrode-pair attachment members. The penetration member allows the first electrode-pair attachment member to enter at a first location, pass through, and exit the tissue at a second location, and subsequently guides the second electrode-pair attachment member to enter and be anchored at least partially within the issue at the first location. The first electrode-pair attachment member subsequently enters at a third location and anchors itself within the tissue, and in a position substantially parallel to the second electrode-pair attachment member. The parallel installation of the first and second attachment members allows the four electrodes to be substantially equidistant with respect to each other.

In yet another preferred embodiment, an electrode attachment member is provided to install four electrodes at the surface of the neuromuscular tissue. The electrode attachment member supports the four electrodes at a distal surface thereof and is configured for attachment to the surface of the neuromuscular tissue to provide an electrical interface between the electrodes and the neuromuscular tissue. The electrode attachment member preferably has a substantially flat distal surface fabricated from a flexible material. This flexibility allows the distal surface to substantially conform to any curvature of the neuromuscular surface. The flexibility also permits the electrode attachment member to be reduced in size to a compact form by rolling, folding, etc. The electrode attachment member may be inserted into the patient while in the compact form through minimally invasive laparoscopic or similar surgical access openings. A cylindrical sleeve member or annular bands may be provided to surround the electrode attachment member to assist in maintaining it in the compact form.

Preferred methods for installation in accordance with the invention include providing an electrode assembly which supports the four electrodes. A further step may include providing a surgical access opening in the patient and laparoscopically introducing the electrode assembly into the patient. A subsequent step may include attaching the electrode assembly to the neuromuscular tissue to provide an electrical interface between the electrode and the tissue.

Once the electrode assembly has been installed, thereby orienting the four electrodes to the tissue, it is possible to begin stimulating the tissue in a novel manner. In a preferred embodiment, a normal generator is provided to generate the stimulating pulses, and a switching matrix is provided under firmware control to control a sequential pair-wise stimulation sequence.

The pair-wise stimulation sequences may include a plurality of options. A first stimulation technique may be a quadrapole sequence, wherein electrode pairs at diagonally opposite corners apply a pulse of the same polarity, and adjacent electrodes apply pulses of opposite polarity. A second stimulation technique may be a sequential quadrature bipole, wherein stimulation pairs consist of electrodes at opposite corners that may sequentially stimulate the tissue. A third stimulation technique may be a sequential quadrature bipole, wherein stimulation pairs consist of adjacent electrode pairs that may sequentially stimulate the tissue.

In a preferred embodiment, the pulse parameters may include the timing and duration of pulses applied according to one of the above sequences. In order to vary these parameters during the treatment period, the neuromuscular stimulator may also include a real time clock and a programmable calendar for tailoring the stimulating waveform parameters over the treatment period. The real time clock supplies data corresponding to the time of day during the treatment period. The programmable calendar stores parameters which refer to the shape of the stimulating waveform. Each of the parameters may be referenced directly or indirectly to the time of day. Circuitry, such as a control circuit, applies the stimulating pulses which are defined by the parameters at the appropriate times of the day during the treatment period.

The real time clock and the programmable calendar allow the stimulating waveform to vary over greater periods of time. For example, the real time clock may supply data corresponding to a week during the time period. Consequently, the waveform may be programmed to apply a different waveform during each particular week in the treatment period. The real time clock may also supply data corresponding to the day of the week during the treatment period. Alternatively, the real time clock may supply data corresponding to a month of the year during the treatment period, such that the waveform may vary from month-to-month as the treatment progresses. Moreover, the real time clock may also supply data corresponding to the day of the month, and/or the day of the year.

Although electrode assemblies are illustrated in the form a pair of elongated bodies or of a patch, certain aspects of the invention are equally applicable to electrode assemblies having other shapes and other methods of installation, as well as alternative four pole stimulation sequences. Briefly summarized, the present invention relates to approaches and methods for electrically stimulating neuromuscular tissue of the viscera of the organ structure, including the gastrointestinal tract by connecting a plurality of electrodes to at least one organ in the gastrointestinal tract of a patient connected at a different location along the peristaltic flow path. Electrical pulses to the organ are provided from a first set of the plurality of electrodes and second electrical pulses to the organ are provided from a second set of electrodes. The electrical pulses provided by the plurality of electrodes are in an independent non-phased relationship for maintaining therapeutic regulation of peristaltic flow through the at least one organ in the gastrointestinal tract while defeating the body's natural tendency for adaption.

Further features of the invention, its nature, and various advantages will be more apparent from the accompanying drawings and the following detailed description of the preferred embodiments.

BRIEF DESCRIPTION OF THE DRAWINGS

FIG. 9 illustrates a data structure for storing parameters for the waveform of a stimulating pulse in accordance with the invention.

FIG. 14 is a simplified view of an apparatus in accordance with an alternative embodiment of the invention.

FIG. 15 is a simplified sectional view of a portion of the apparatus of FIG. 14, illustrating a stage in the installation of the apparatus in accordance with the invention.

FIG. 16a is a simplified elevational view of the apparatus of FIG. 14 installed in the patient in accordance with the invention.

FIG. 16b is a simplified sectional view of the apparatus of FIG. 16a.

FIG. 23 is a view of an apparatus according to an alternate adaption defeating embodiment in accordance with the invention.

DETAILED DESCRIPTION OF THE PREFERRED EMBODIMENTS

Figure 2:
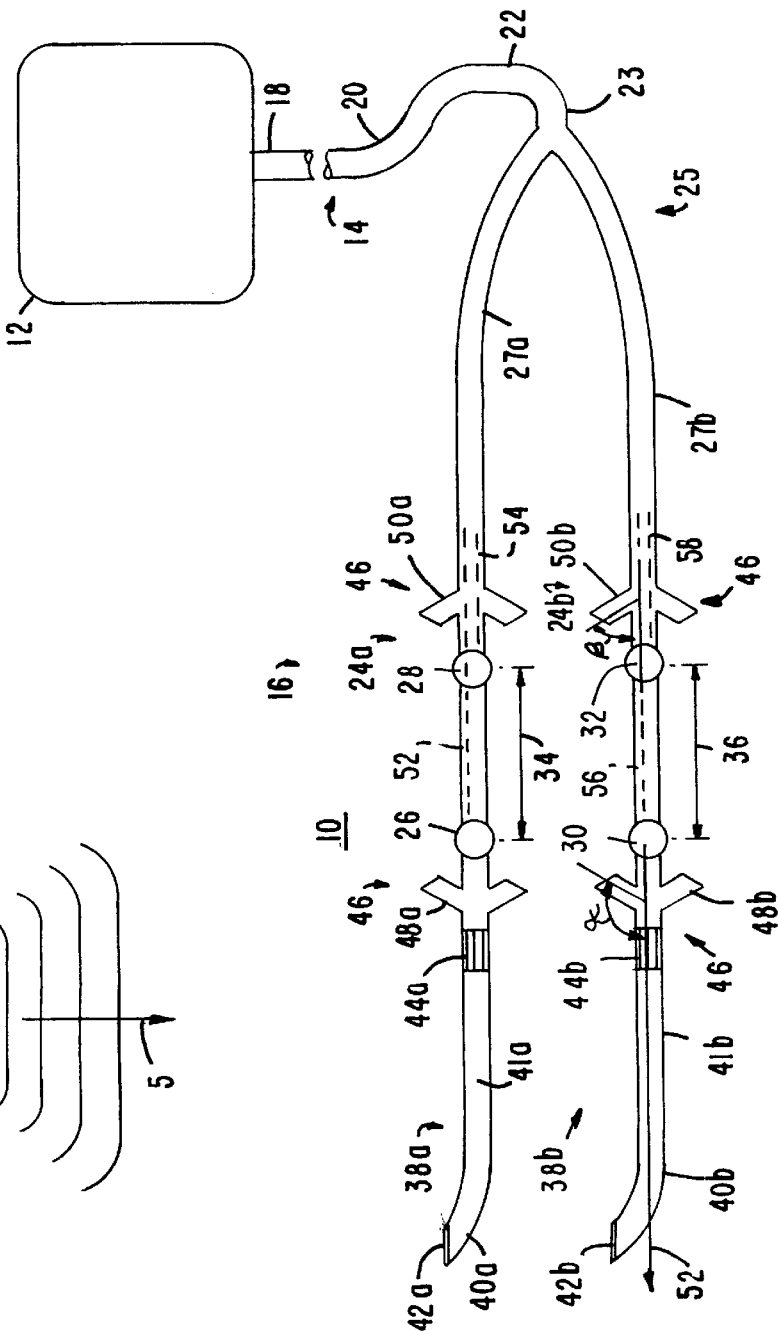
FIG. 2 is a simplified view of an apparatus in accordance with the invention.

An improved neuromuscular stimulator is illustrated in FIG. 2, and designated generally with reference number 10. The stimulator 10 includes an implantable pulse generator 12, a lead system 14 and an electrode assembly, or implant device 16. The implantable pulse generator 12 provides a series of electrical pulses to and/or electrical monitoring of the tissue of the viscera. It is understood that the viscera may include any organs of the human torso, and primarily those of the abdominal region. For example, the principles in accordance with the invention are applicable to such body organs as the liver, pancreas, and the gastrointestinal tract (not shown in FIG. 2). Suitable pulse generators are described in commonly-assigned U.S. Pat. No. 5,423,872 to Cigaina and concurrently-filed Gordon U.S. patent application Ser. No. 09/466,387, filed Dec. 17, 1999, both of which are incorporated by reference in their entirety herein. The implantable pulse generator 12 may be surgically implanted subcutaneously in the abdominal wall. The electrical stimulation lead 14 includes a proximal connector end 18 to interface with the implantable pulse generator 12, a medial lead body portion 20, and a distal end portion 22, for electrical connection with the electrode assembly 16.

According to the preferred embodiment, the electrode assembly, or implant device, 16 has a bifurcated configuration, which may include a pair of elongated body portions, such as substantially identical electrode attachment members 24a and 24b. Electrode attachment member 24a supports a pair of electrodes A 26 and B 28, and electrode attachment member 24b supports a pair of electrodes C 30 and D 32.

Electrodes A 26 and B 28 are spaced apart a distance 34 of about 0.5 cm to about 2 cm. Similarly, electrodes C 30 and D 32 are spaced apart a distance 36 of about 0.5 cm to about 2 cm. In a preferred embodiment, distance 34 and distance 36 are equal. The electrode assembly 16 may have a bifurcated structure, which is dimensioned such that the resulting spacings 55 and 57 between electrodes on opposite electrode attachment members 24a and 24b after implantation are approximately the same as spacings 34 and 36, thus achieving quadrature symmetry of the four electrodes (see FIG. 5). This bifurcated structure is preferably achieved by a bridging portion 25 having a first end portion 23 electrically connected with the pulse generator 12 and the lead 14, and a pair of second end portions 27a and 27b, each of which may be connected to a respective electrode-pair attachment member 24a/24b. Although FIG. 2 may not necessarily be drawn to scale, second end portions 27a and 27b are preferably dimensioned with sufficient length to allow the physician to independently install electrode-pair attachment members 24a and 24b in the tissue.

Each electrode-pair attachment member 24a and 24b includes penetration mechanism 38a and 38b to pass through the tissue in which the electrodes A 26, B 28, C 30, D 32 are desired to be implanted. Each of penetration mechanisms 38a and 38b may include a noncutting curved portion 40a and 40b, a noncutting linear portion 41a and 41b, and a distal cutting end portion 42a and 42b. Each penetration mechanism 38a and 38b is respectively connected to the electrode attachment member 24a and 24b by a connecting or "quick-release" mechanism 44a and 44b. Connecting elements 44a and 44b and elongated body portions 24a/24b are preferably formed from a silicone material, e.g., a surgical-grade silicone or other biocompatible material having similar stress characteristics. Connecting elements are manufactured having flexibility characteristics to permit relative movement of the penetration mechanism 38a/38b with respect to elongated body portions 24a/24b. The length of connecting elements are adjusted to permit angling and flexibility without harming the electrical conduction components located within the elongated body portions 24a/24b. Preferably connecting elements 44a/44b are radiopaque, and may be severed by the physician during the implantation process to separate the penetration mechanism 38a/38b from the electrode attachment member 24a/24b. As will be described in greater detail hereinbelow, a preferred means of severing the connecting members 44a/44b may include the use of endoscopically introduced scalpel or scissors.

Electrodes A 26 and B 28 as well as C 30 and D 32 may be anchored with respect to the patient's tissue by securing mechanisms, such as securing members 46. Securing members 46 are preferably fabricated from a biocompatible material, such as, for example, silicone, and may consist of first tines 48a/48b and second tines 50a/50b. Generally, both the first 48a/48b and second tines 50a/50b each define a set of at least two in number; preferably each set of tines are three to five in number. In the preferred embodiment, first tines 48a/48b may be leading tines, that is, tines 48a/48b are preferably flexible and define an obtuse angle α with respect to the direction of travel 52. This configuration aids in the passage of electrode attachment member 24a/24b in the direction 52, while inhibiting movement in the opposite direction. Preferably, the first tines 48a/48b have a diameter of about 1 mm and a length of about 3 mm and may enter the tissue (e.g., at the "entrance" site), may penetrate the thickness of the tissue to be stimulated, and exit on the opposite side (e.g., the "exit" site of the tissue). Once through the tissue, first tines 48a/48b may provide contact with the exit site of the tissue, and inhibit movement of the electrode attachment member 24a/24b opposite to direction 52.

Second tines 50*a*/50*b* may define an acute angle β with direction 52. In operation, second tines 50*a*/50*b* do not penetrate the thickness of the tissue to be stimulated. Rather, they may provide contact with the entrance site of the tissue, and therefore inhibit movement of electrode positioning member in direction 52. This configuration is useful in securing electrode attachment member 24*a*/24*b* in the implanted tissue to prevent dislodgement after installation by locking or anchoring the tissue between first tines 48*a*/48*b* and second tines 50*a*/50*b*, as will be described in greater detail hereinbelow. The distance between the first tines 48*a*/48*b* and the second tines 50*a*/50*b* may vary as deemed necessary by the physician, and may depend on the desired distance 34/36 between the electrodes and the thickness of the tissue to be stimulated. Preferably, the linear portion 41*a*/41*b* of penetration mechanism 38*a*/38*b* may have a length that is at least equal to the distance between first tines 48*a*/48*b* and second tines 50*a*/50*b*.

The base materials for the electrodes A 26,18 28 and C 30, D 32 may include any material typically used for electrodes such as, e.g., stainless steel, platinum, platinum-iridium alloys, iridium oxide, titanium and the like. The electrodes A 26,18 28 and C 30, D 32 may be in an uncoated state or may be coated with materials such as iridium oxide or titanium nitride, or the electrodes may be platinized or carbonized. Each of the conductors A 26,18 28, C 30, D 32 are respectively electrically connected to a distinct conductor 52/54/56/58, each of which is connected electrically to the pulse generator 12 at the proximal end. The conductors may be surrounded by an electrically insulative material to isolate the non-common conductors from each other, as necessary, and to isolate the conductors 52/54/56/58 from the physiological environment. The lead body 20 may include a plurality of conductive coils (not shown) isolated within an electrically insulative material such as silicone elastomer. The lead body 20 may utilize a coaxial or parallel conductor design. The conductive coils of the lead body may electrically connect the proximal terminations of the lead 18 to their corresponding distal electrode or electrodes A 26,18 28, C 30, D 32.

Installation of the Preferred Embodiment

The above-described configuration of the electrodes and electrode assembly provides for a simple, minimally-invasive installation procedure in accordance with the invention. According to an early stage of the invention, the approximate location of the gastrointestinal tissue is located by the physician. An incision is made in the patient in the surface of the skin above the operative site. According to a preferred embodiment, an obturator device may be used to provide the incision and install a trocar. The process of insufflation may be used, wherein an inert gas such as carbon dioxide is introduced under pressure, to enlarge the body cavity and provide improved visualization and access within the body cavity. A series of trocars may be installed through the patient's skin which allow access for surgical instrumentation while maintaining insufflation pressure. A laparoscope or similar remote viewing apparatus may be inserted through one of the trocars in order to allow viewing of the process of attachment of the electrode assembly to the tissue, such as the stomach tissue, in this example.

The electrode assembly 16 is preferably passed through the trocar in a compacted form. The bridging portion 25 is preferably flexible, which facilitates the process of placing the electrode assembly in the compacted form. For example, the electrode attachment members 24*a*/24*b* may be placed in approximation with one another. The electrode assembly 16 may be contained within a sleeve that is passed through a trocar. It is contemplated that the sleeve may be omitted when the electrode assembly is passed through the trocar or other access opening.

After trocar passage, the electrode assembly may be freed from the sleeve by mechanical means. For example, mechanical grasping apparatus, such as a grasper, may be used to hold the electrode assembly with grasping jaws to remove the electrode assembly from an end portion of the sleeve. According to an alternative embodiment, the electrode assembly is pushed out of the sleeve by advancing an apparatus, such as a blunt instrument, a plunger, a blunt dissection device, or a balloon catheter device.

Figure 3:
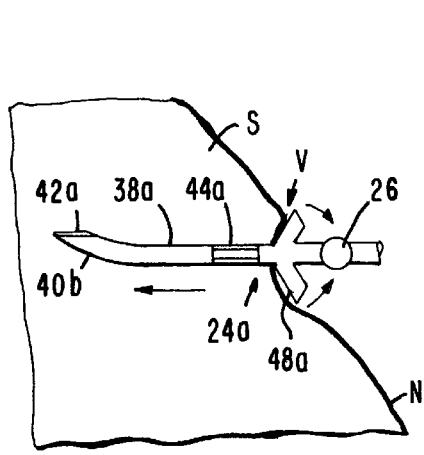
FIG. 3 is a simplified sectional view of a portion of the apparatus of FIG. 2, illustrating a stage in the installation of the apparatus in accordance with the invention.

A stage of attachment of the electrode assembly to the tissue follows. The attachment may be achieved in several ways. As illustrated in FIG. 3, the penetration mechanism 38 passes through the tissue S. More particularly, distal cutting end portion 42*a* pierces the tissue S at entrance site V of the outer stomach wall in the case of a gastric stimulator and is advanced as indicated by the arrow. First tines 48*a*, as described above, are angled to facilitate passage as shown into the tissue. Tines 48*a* are preferably resilient and may deflect towards parallelism with the electrode attachment member 24*a* during insertion. Preferably, forceps, such as endoscopic forceps, may be used by the physician to advance the electrode mounting member 24*a* into the tissue. As illustrated in FIG. 3, cutting end portion 42*a* preferably enters the tissue S at entrance site V at an angle to facilitate exiting the surface N, as will be described in greater detail below.

Figure 4A:
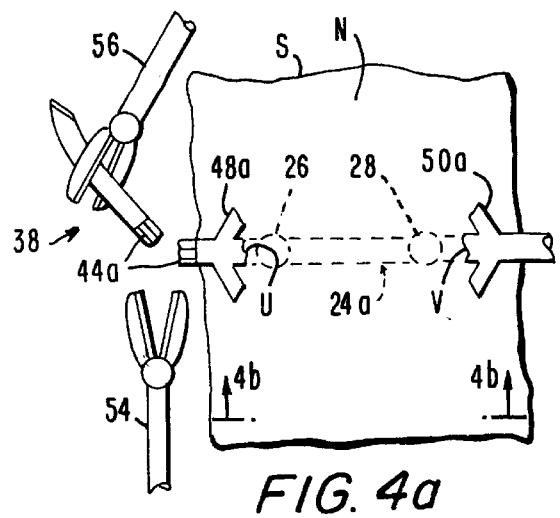
FIG. 4a is a simplified elevational view of the apparatus of FIG. 2 and additional apparatus, illustrating a later stage in the installation of the apparatus in accordance with the invention.
Figure 4B:
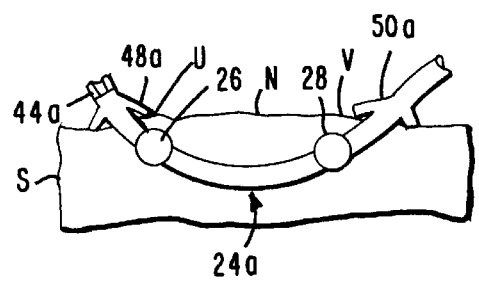
FIG. 4b is a simplified sectional view of the apparatus of FIG. 4a, illustrating a later stage in the installation of the apparatus in accordance with the invention.

As illustrated in FIGS. 4(*a*) and 4(*b*), electrode mounting member 24*a* is advanced such that connecting member 44*a* and first tines 48*a* pass through the tissue S and subsequently protrude from the outer surface N at the exit site U of the tissue S.

Electrode attachment member 24*a* may be sufficiently flexible in order to pass the member in the tissue S at location V and subsequently exit at location U at the same surface N. First tines 48*a* may resiliently move towards the undeflected position, such as illustrated in FIG. 2, above, and inhibit movement of electrode attachment member 24*a* out of the tissue S. Second tines 50*a* may be axially spaced from first tines 48*a* such that they abut the entrance site V of the tissue S and inhibit further movement of electrode attachment member 24*a* into the tissue S. In this position, the tissue S is located between the two sets of tines 48*a* and 50*a*. Moreover, the electrode attachment member 24 is effectively anchored in place by tines 48*a* and 50*a*. Electrodes A 26 and B 28 are thus positioned in the tissue S.

The penetrating mechanism 38 may be separated from the electrode attachment member 24*a* by severing the connecting member 44*a*. Preferably, a cutting instrument, such as endoscopic scissors 54, may be used to sever connecting member 44*a*. A grasping mechanism, such as endoscopic graspers 56, may be used to hold penetrating mechanism during the severing of connecting member 44*a*, and during removal thereof from the operative site.

Figure 5:
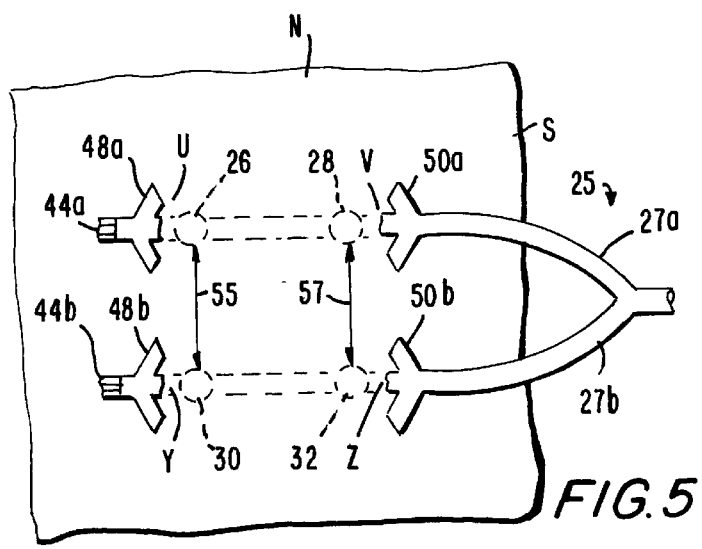
FIG. 5 is a simplified sectional view of the apparatus of FIG. 2 installed in the patient in accordance with the invention.

As illustrated in FIG. 5, the electrode attachment member 24*b* (illustrated in dashed line) is shown installed in tissue S. Second end portions 27*a* and 27*b* of bridging structure 25 are sufficiently long to allow the physician to maneuver and install electrode-pair attachment member 24*b* in the tissue S with penetrating mechanism 38*b*. The installation of electrode attachment member 24*b* is performed substantially as described in FIGS. 3–4 with respect to electrode attachment member 24*a*. First tines 48*b* are positioned adjacent the exit site Y of the tissue, and second tines 50*b* are positioned adjacent the entrance site Z. Following installation, electrode attachment member 24*b* is substantially parallel to electrode attachment member 24*a*, and electrodes A 26,18 28 are spaced apart from electrodes C 30, D 32 by substantially equal distances 55 and 57, such as, 0.5 cm to 2.0 cm, which are substantially the same distance as distance 34 and 36, shown in FIG. 2.

Figure 6:
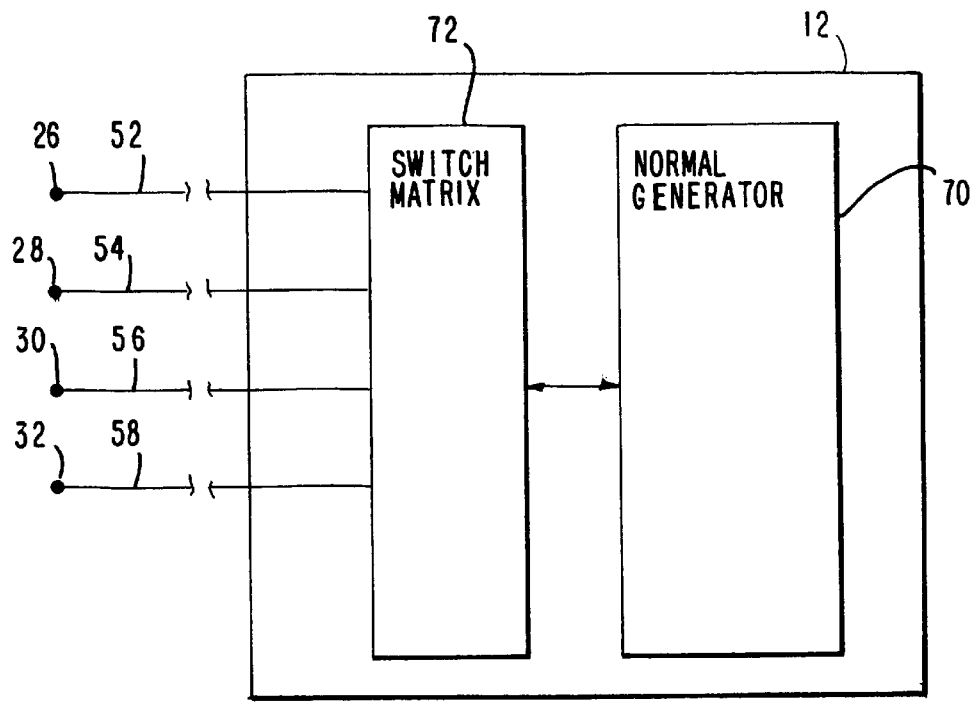
FIG. 6 is a simplified schematic view of a component of the apparatus in accordance with the invention.

FIG. 6 illustrates a preferred embodiment of circuitry in pulse generator 12 for applying stimulation pulses to the electrodes A 26, B 28, C 30, and D 32. In accordance with this embodiment, each electrode A 26, B 28, C 30, and D 32 is connected respectively to a lead 52/54/56/58. A typical generator well-known in the art, such as generator 70, is provided to generate the electrical pulse stimulation of the electrodes. These pulses are generated in a predetermined sequence under firmware control as will be described in greater detail below. Switching matrix 72 receives instructions from generator 70 and applies the stimulating pulse to the appropriate set of electrodes with appropriate polarity to stimulate the tissue.

Each individual switch of matrix 72 is normally open and can be connected either to the positive or negative output terminals of the generator or left open during a stimulation pulse as controlled by the timing sequence processor.

Figure 7A:
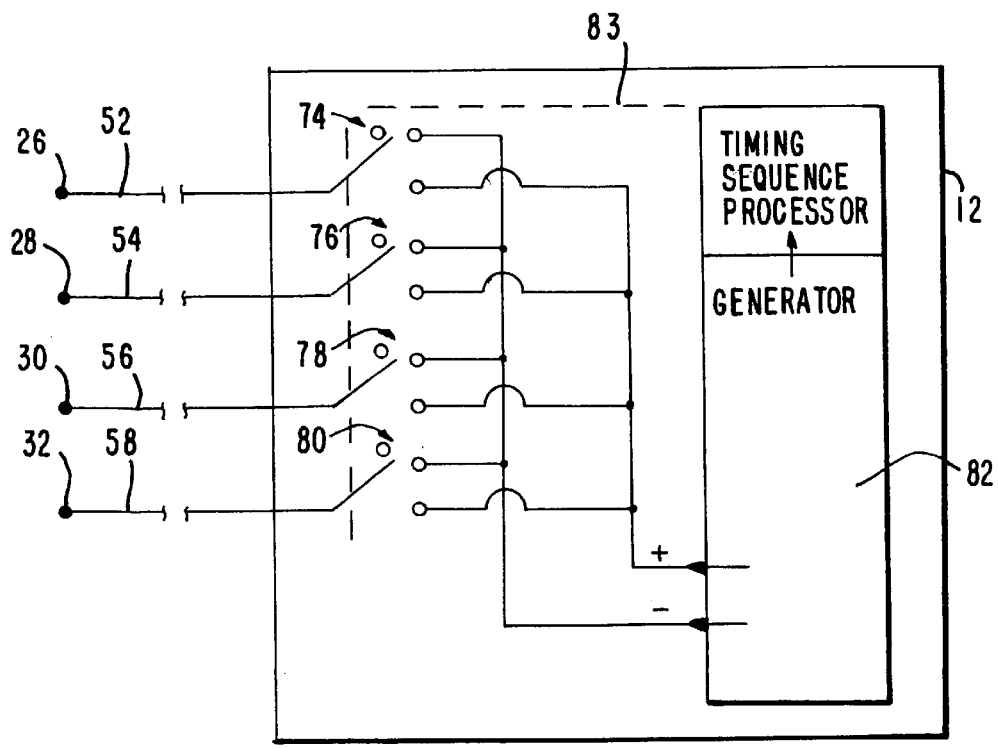
FIG. 7a is a simplified schematic view of a component of the apparatus of FIG. 2 in accordance with an alternative embodiment of the invention.

FIG. 7*a* illustrates another embodiment of the circuitry in pulse generator 12. As described with respect to FIG. 6, above, each electrode A 26, B 28, C 30, and D 32 is respectively connected to a lead 52/54/56/58. Four triple-pole outputs (corresponding to open, + polarity, and − polarity) 74/76/78/80 operate under firmware control of the timing sequence processor 82 on line 83. Voltage source 84 may be current-controlled or voltage-controlled.

Figure 7B:
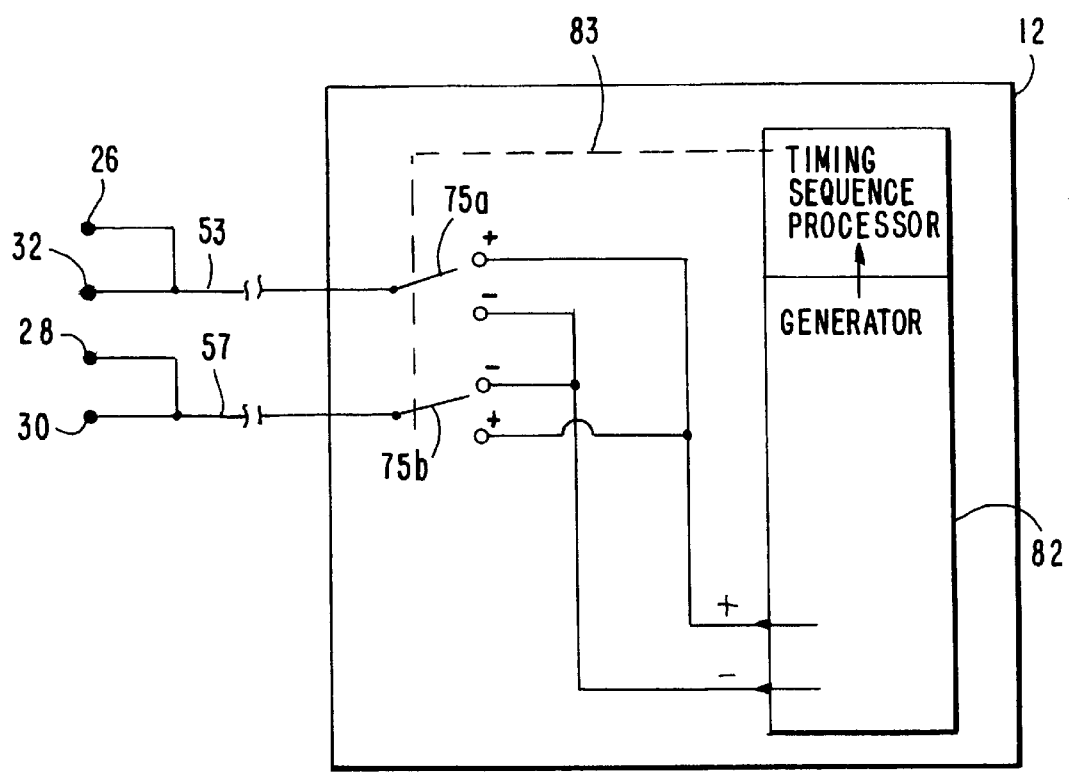
FIG. 7b is a simplified schematic view similar to FIG. 7b in accordance with another alternative embodiment of the invention.

FIG. 7*b* illustrates another alternative embodiment of the circuitry in pulse generator 12. Electrodes A 26 and D 32 are both connected to a lead 53 on a first conduction path. Similarly, electrodes B 28 are C 30 are connected to a lead 57 on a second conduction path. The number of switches may thus be reduced from four independent switches to a pair of double-pole switches 75*a*/75*b* which operate in tandem to provide a quadrapole.

Stimulation Techniques and Programming

The generator 70 (FIG. 6) in concert with the timing sequence processor 83 (FIG. 7) may be programmed to provide stimulation pulses to the tissue. The variations in pulses allow the four electrodes, electrode A 26, electrode B 28, electrode C 30, and electrode D 32 to stimulate the tissue individually, and in any combination. The ability to vary the stimulation applied to tissue, such as that of the stomach, is important to entrain the tissue. A characteristic of this tissue, as distinguished from heart tissue, is that the stomach tissue may become fatigued by constant stimulation. Thus the ability to change the direction and intensity of stimulation may prevent or reduce such fatigue. In the description of the stimulation techniques and sequences which follows, it is presumed that there are four electrodes which may be independently controlled to stimulate the tissue. The four electrodes are substantially equidistantly spaced with respect to one another, thereby forming a substantially square configuration, with each electrode located at one of four "corners" (see, e.g., electrodes A 26, B 28, C 30, and D 32 in FIG. 5). In order to simplify the following discussion, the term "adjacent electrode pairs" shall refer to electrodes located in adjoining corners of the configuration, e.g., electrodes A 26 and B 28 are adjacent pairs, and electrodes A 26 and C 30 are likewise adjacent pairs. The term "diagonal electrode pairs" or "opposite electrode pairs" shall refer to electrodes located in opposite corners of the configuration, which are spaced further apart than adjacent pairs. For example, electrodes A 26 and D 32 are diagonal pairs, and electrodes B 28 and C 30 are likewise diagonal pairs.

An option for programming the electrodes is a quadrapole stimulation configuration. In this case, first diagonal electrode pairs of electrodes A 26 and D 32 may have a positive voltage, while second diagonal electrode pairs of electrodes B 28 and C 30 may simultaneously have a negative voltage. Similarly, first diagonal electrode pairs of electrodes A 26 and D 32 may have a negative voltage, while second diagonal electrode pairs of electrodes B 28 and C 30 may simultaneously have a positive voltage.

Another option may be a sequential quadrature bipole configuration. According to this option, a sequence involving two sets of pulses is defined. A first diagonal electrode pair is defined by electrodes positioned diagonally opposite to each other, e.g., electrode A 26 and electrode D 32 defining a first diagonal electrode pair and electrode B 28 and electrode C 30 defining a second diagonal electrode pair. During the first set of pulses in the sequence, electrical stimulation is applied across the first diagonal electrode pair, i.e., electrode A 26 applies a positive pulse and electrode D 32 simultaneously applies a negative pulse. During the second set in the sequence, electrical stimulation is applied across the second diagonal electrode pair, i.e., electrode B 28 applies a positive pulse and electrode C 30 applies a negative pulse. Typically, this sequence of two sets of pulses may be repeated several times during the treatment period. A variation of the above sequential quadrature bipole sequence may involve four sets of pulses in the sequence. The first and second sets of pulses in the sequence, are the same as described above, i.e., in the first set of pulses applied across the first diagonal electrode pair, electrode A 26 is positive and electrode D 32 is negative; and during the second set applied across the second diagonal electrode pair, electrode B 28 is positive and electrode C 30 is negative. During the third set of pulses in the sequence, electrical stimulation is applied across the first diagonal electrode pair such that electrode D 32 is now positive and electrode A 26 is simultaneously negative. During the fourth set in the sequence, electrical stimulation is applied across the second diagonal electrode pair such that electrode C 30 is positive and electrode B 28 is negative. This sequence of four sets of pulses may be repeated several times during the treatment period.

Another alternative option with regard to applied pulses is a sequential semi-quadrature bipole. This option is a sequence of four steps of applied pulses. In the first step, electrical stimulation is applied across a first adjacent electrode pair such that electrode A 26 is positive and simultaneously electrode B 28 is negative. In the second step, electrical stimulation is applied across a second adjacent electrode pair such that electrode B 28 switches to positive and simultaneously electrode D 32 is negative. During the third step, electrical stimulation is applied across a third adjacent electrode pair such that electrode D 32 switches to positive and simultaneously electrode C 30 is negative. During the fourth step, electrical stimulation is applied across a fourth adjacent electrode pair such that electrode C 30 switches to positive, and electrode A 26 is negative. The sequence of four steps may be repeated during treatment. An alternative sequential semi-quadrature bipole sequence also involves four steps in the sequence. In the first step, electrical stimulation is applied across a first adjacent electrode pair such that electrode A 26 is positive and simultaneously electrode B 28 is negative. In the second step, electrode B 28 remains negative and simultaneously electrode D 32 is positive. During the third step, electrode D 32 remains positive and simultaneously electrode C 30 is negative. During the fourth step, electrode C 30 remains negative, and electrode A 26 is positive. This sequence may also be repeated during the treatment.

The above-described sequences, i.e., quadrapole, sequential quadrature bipole, and the sequential semi-quadrature bipole, all utilize the placement of four electrodes in the tissue, and the ability to vary the placement and polarity of the pulses. In addition, another parameter that may be varied is the pulse timing scheme, which concerns the duration in which the sequences are applied to the tissue. According to one timing scheme, pulses having a 40 Hz (25 milliseconds) interval are applied in a burst lasting approximately 2 seconds. According to a second timing scheme, a train of pulses is applied, wherein the pulses are closer than the 40 Hz interval pulse train described above.

According to a third timing scheme, each step in the sequence is applied and held for a specified duration, separated by a specified duration in which no stimulating pulses are applied. A typical timing sequence may involve a two-second period in which pulses may be applied, and a three-second period in which no pulses are applied. For example, for the sequential quadrature bipole sequence, electrode A 26 is positive and electrode D 32 is negative for a two second interval of pulses. No pulses are applied for three seconds, and then electrode B 28 is positive and electrode C 30 is negative for a subsequent two second interval of pulses. An additional three second period follows in which no pulses are applied, and the sequence may repeat.

Figure 8:
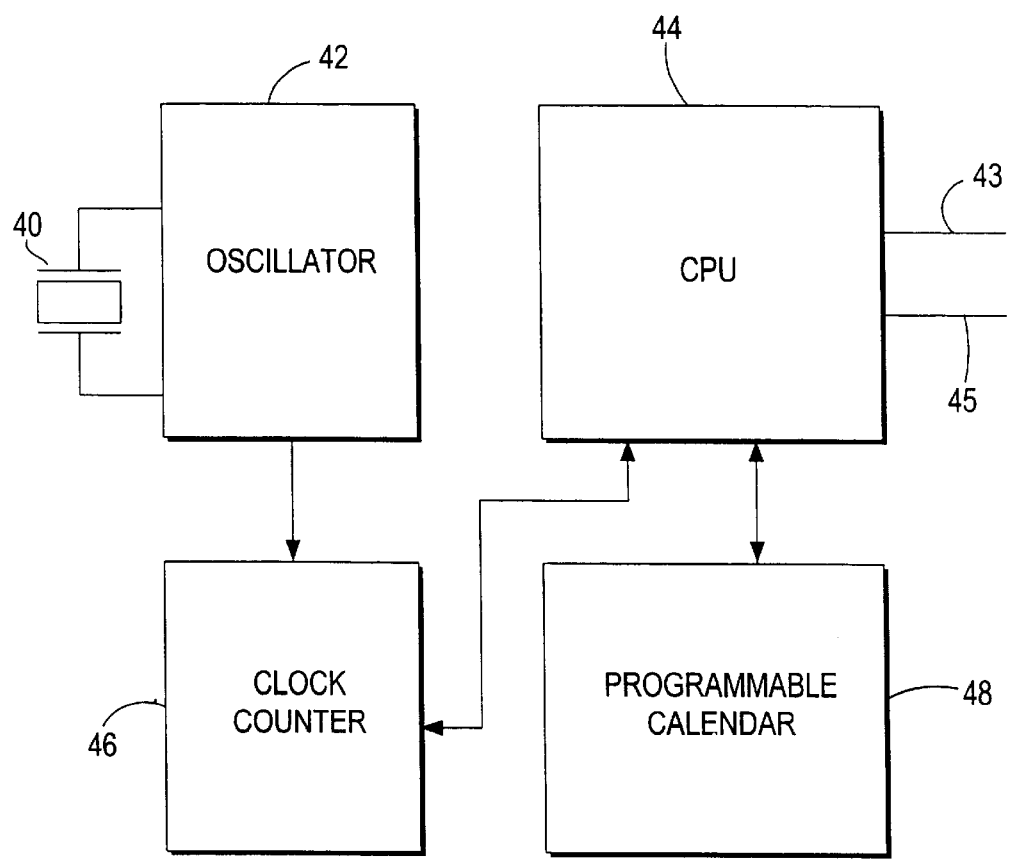
FIG. 8 is a simplified schematic view of a component of the apparatus of FIG. 2 in accordance with the invention.

The fourth timing scheme allows a great deal of flexibility wherein both the sequence type and the duration of specific steps may vary over the treatment period. Timing features and data structures for storing pulse parameters are described in Gordon U.S. patent application Ser. No. 09/466,387, filed Dec. 17, 1999, which is incorporated by reference in its entirety herein. The timing features of generator 12 are illustrated in FIG. 8. By using a crystal 92 to control oscillator 94 (which may be either internal component of processor 96 or a separate component), accuracy is achieved by a real-time clock counter 98. Typically, a 32 or 100 kilohertz crystal clock may be used to provide timing. Stimulation pulse width is typically 100 to 500 microseconds (10 to 50 oscillations of 100 kilohertz clock), and the pulse interval may be 25 milliseconds or 2500 clock oscillations. The "on time," i.e., the period in which the pulses are applied, may be two seconds (200,000 oscillations) for this waveform, and the "off time," i.e., the period in which no pulses are applied, may be three seconds. It is useful to synchronize time inside the processor 96. A programmable storage device, such as programmable calendar 100, can be programmed to store the parameters that define the above pulse train. The parameters are output on line 97 for use by the generator 70 (FIG. 6) or the timing sequence processor 82 (FIG. 7) or control circuit in determining the wave shape of the stimulating pulse. The parameters correspond to particular times during the treatment. Medical observations suggest that food intake, digestion and other gastrointestinal functions are circadian, that is, they operate on a 24 hour daily cycle. There are certain periods during the day when gastric functions are less active than other times of the day. The programmable calendar 100 can therefore provide increased stimulation at certain hours of the day, and decreased stimulation at other hours of the day. Among other benefits, device longevity may be increased due to the energy saving of this programming. Thus the electrode assembly 16 may deliver stimulation pulses for a fraction of each hour while the patient is awake. The programmability of calendar 100, described below, allows the application of longer-term circadian variations which may likewise be beneficial to the patient and extend battery life.

Figure 10:
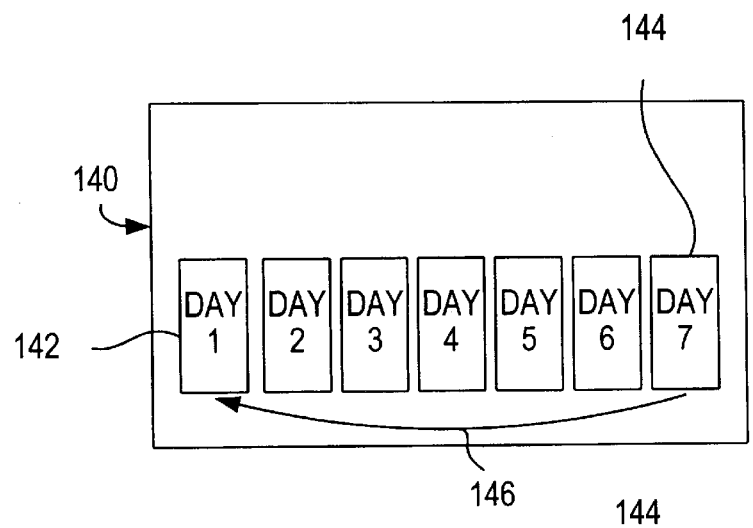
FIG. 10 illustrates another data structure in accordance with the invention.

A plurality of pulse train parameters may be stored in memory associated with the programmable calendar 100. Sample data 110 for a treatment period is shown in FIG. 9. The data 110 may be for a 24-hour period, such as "day one" 112, which may include calendar information 114. The pulse trains may be stored as cycles 116. For example, pulse train parameters may include start times 118, stop times 120, the pulse width 122, the pulse interval 124, the duration of the applied pulses (the "on" period) 126, or the duration period in which no pulses are applied (the "off" period) 128, and the voltage of the pulse or the pulse height 130. The polarity of each of the electrodes A 26, B 28, C 30 and D 32 may be specified, as fixed polarities, or alternatively as a sequence of polarities, during this interval. As shown in FIG. 9, electrode A 26 may be designated with a positive polarity 132, electrode D 32 may be designated with a negative polarity 138, and electrodes B 28 and C 30 may be inactive during this cycle, data points 134 and 136. The programmable calendar 100 receives data from the clock 98 concerning the time-of-day and the date. Programmable calendar 100 can obtain the associated parameters from the data 110 and supply them to the processor 96, accordingly. The "date" associated with the treatment may vary, depending on the expected duration of the treatment. For example, in data format 140 (FIG. 10), the data may correspond to the day of week (e.g., "day one" 142 through "day seven" 144). Each of the data structures for day one 142 through day seven 144 may be similar to data 110. The programmable calendar 100 may function on a seven-day cycle wherein programmable calendar accesses day one after day seven in a continuous loop 146. Thus, each day of the week could have a particular sequence of stimulating pulse train parameters. As a result, the pulse train is programmed to stimulate the stomach tissue in the same way on the same day of each week.

Figure 11:
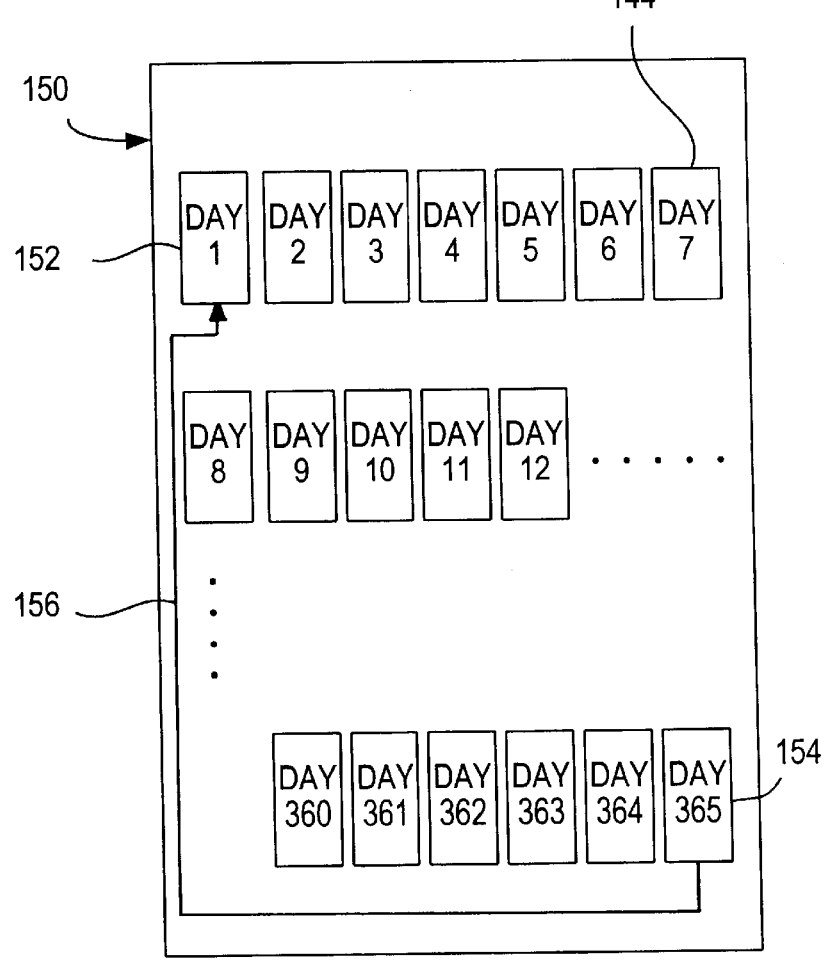
FIG. 11 illustrates yet another data structure in accordance with the invention.
Figure 12:
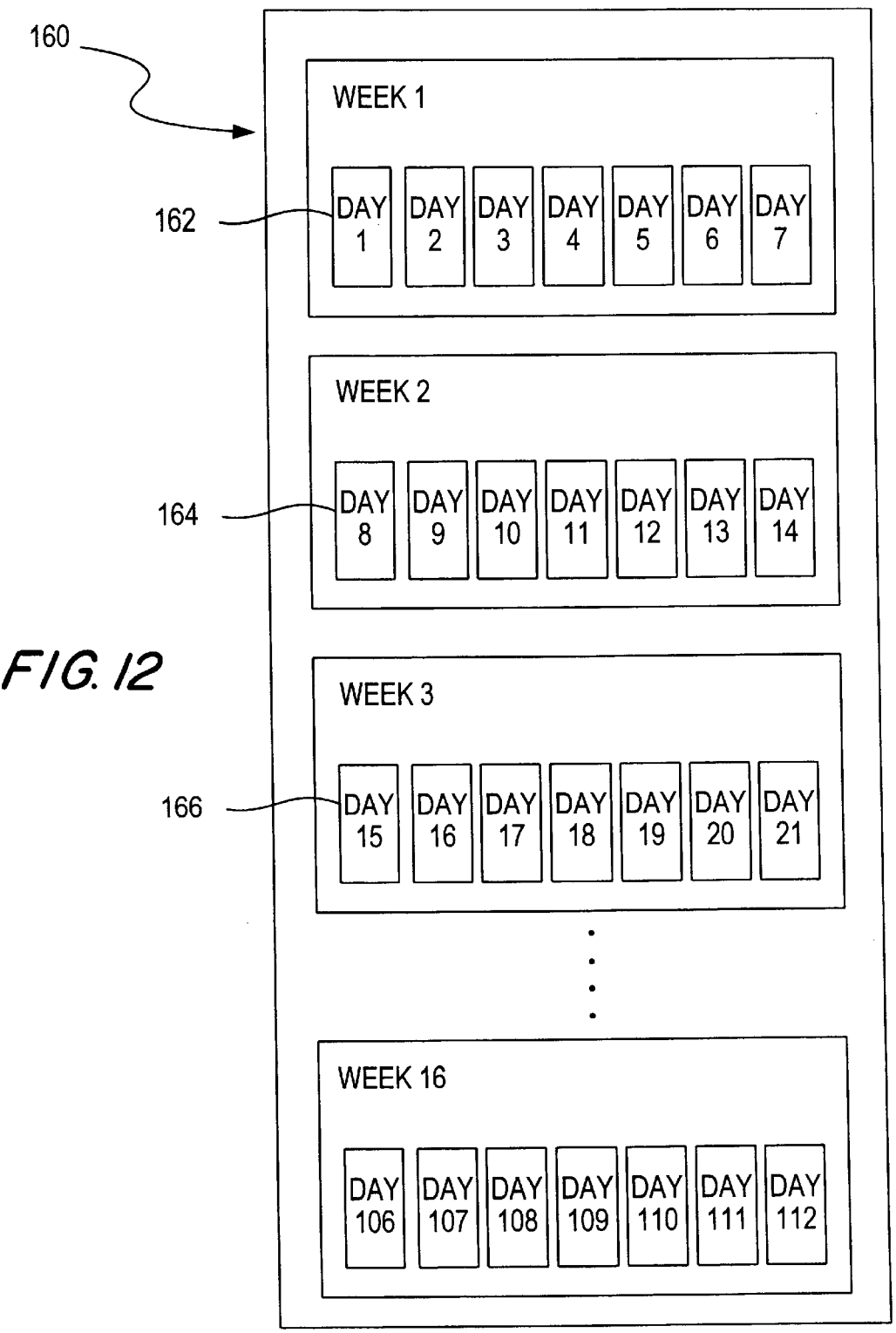
FIG. 12 illustrates still another data structure in accordance with the invention.

As illustrated in FIG. 11, the data format 150 may refer to a simple, numbered day in a periodic sequence of days, such as the numbered days of the year (i.e., "day one" 152 through "day 365" 154), or the numbered days within a month (e.g., "day one" through "day 31", not shown). The calendar 100 would then cycle back to the first data point as indicated by arrow 156. As illustrated in FIG. 12, the data format 160 may be hierarchical and thus may recognize intermediate time periods, such as weeks 162 and/or months (not shown) within a treatment period. For example, it may recognize that the treatment is at "week two" 164 or "week three" 166, in addition to the elapsed number of days. The calendar 100 could be programmed to so that the pulse generator 10 is turned off for a number of weeks. The generator may then be turned on one day a week. During the next week, the generator may be turned on for two days a week, etc. Each sequence of cycles (see FIG. 9) within a given "on" day, could also be different from the previous "on" day.

Figure 1:
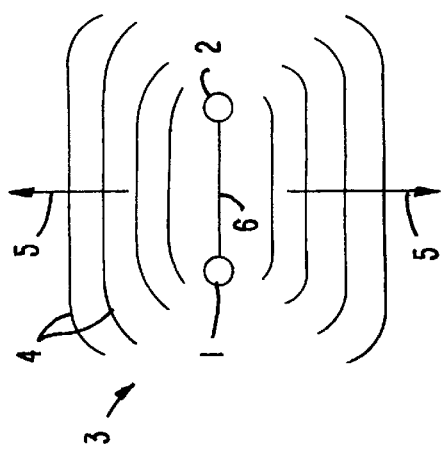
FIG. 1 is a simplified view of a typical prior art stimulating electrode pair and associated electric field gradient pattern.
Figure 13:
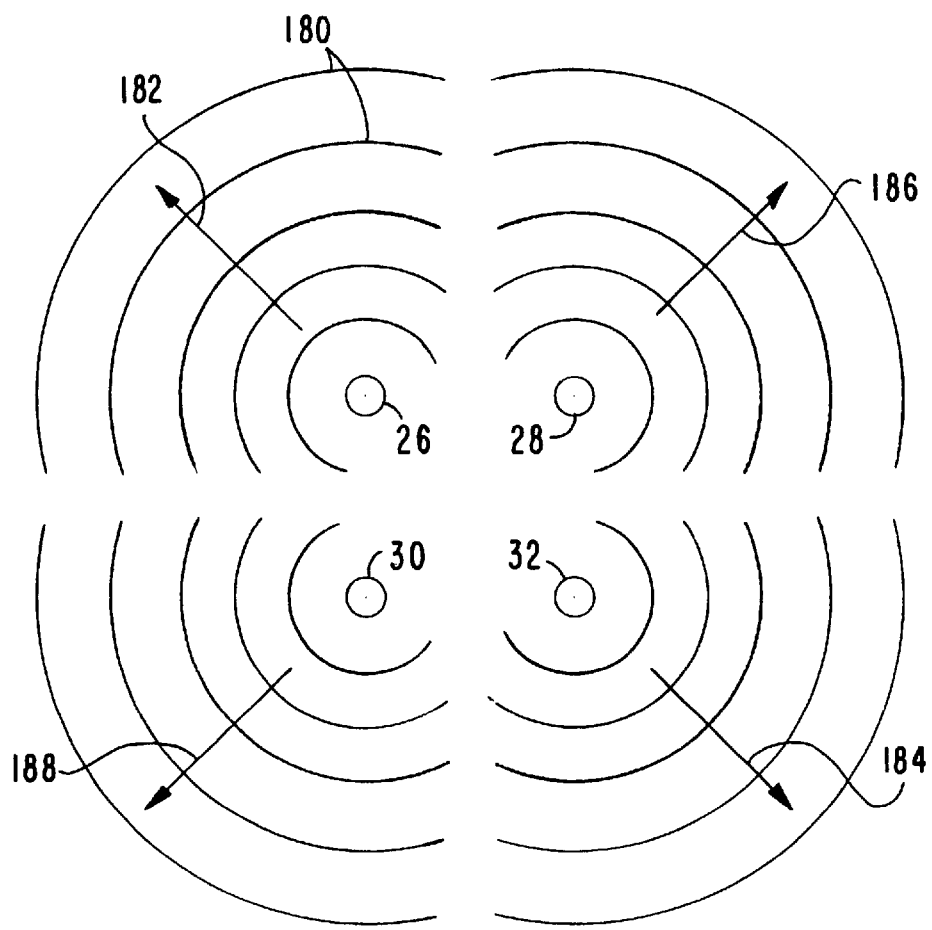
FIG. 13 is a simplified view of the stimulating waveform propagation provided by the apparatus in accordance with the subject invention.

FIG. 13 illustrates the propagation of stimulation waves provided by placement of electrodes A 26, B 28, C 30, and D 32 in the tissue. The tissue stimulation 180 propagate generally radially outwardly, e.g., directions 182/184/186/188, from the electrodes. In contrast with the substantially one-dimensional propagation (see FIG. 1) of the prior art, the electrodes in accordance with the invention generate stimulating pulses which cover a larger area of tissue. This may result in better entrainment of muscle tissue stimulated thereby. Moreover, the sequential stimulation of electrodes A 315, B 317, C 319 and D 321, e.g., the quadrapole, sequential quadrature bipole, or sequential semi-quadrature bipole sequences described above, may be used to vary the direction of the stimulation, e.g., propagation in directions 182 and 184, followed by propagation in directions 186 and 198. This may be helpful to stimulate tissue which responds to stimulation in preferred directions.

Alternative Embodiment

An alternative embodiment of the neuromuscular stimulation electrode system is illustrated in FIG. 14, and designated generally with reference number 200. The stimulator 200 is substantially similar to stimulator 10 with the differences noted herein, and includes an implantable pulse generator 212, a lead system 214, and an electrode assembly 216. The electrical stimulation lead 214 includes a proximal connector end 218 to interface with the implantable pulse generator 212, a medial lead body portion 220, and a distal end portion 222, for electrical connection with the electrode assembly 216.

According to the alternative embodiment, the electrode assembly 216 does not have the bifurcated configuration of electrode assembly 16, having electrode attachment members 24a/24b in parallel (FIG. 2). In contrast, electrode assembly 216 may include a pair of substantially identical electrode attachment members 224a and 224b arranged in a series configuration. A bridging portion 225 may connect electrode attachment member 224a with electrode attachment member 224b. Bridging portion 225 is not necessarily represented to scale; however, it is understood that bridging portion 225 is sufficiently long to permit the physician to maneuver and install electrode-pair attachment members 224a and 224b, as described in greater detail hereinbelow. Moreover, electrode assembly 216 includes a single penetration mechanism 238 to pass through the tissue in which the electrodes A 226, B 228, C 230, D 232 are desired to be implanted. Penetration mechanism 238 may include a curved portion 240 and a distal cutting end portion 242. Penetration mechanism 238 is connected to the electrode attachment member 224a by a connecting member 244, substantially identical to connecting member 44 (FIG. 2).

Electrodes A 226 and B 228, and electrodes C 230 and D 232 may be anchored with respect to the patient's tissue by securing members 246. Securing members 246 substantially similar to securing members 46 may consist of first tines 248a/248b and second tines 250b. In the preferred embodiment, first tines 248a/248b may be leading tines, that is, tines 248a/248b define an obtuse angle with respect to the direction of travel 252 and 253, respectively. This configuration aids in the passage of electrode attachment member 224a in the direction 252 and electrode attachment member 224b in the direction 253, while inhibiting movement in the opposite direction.

Second tines 250b may define an acute angle with direction 253. In operation, second tines 250b do not penetrate the thickness of the tissue to be stimulated, but may provide contact with the entrance site of the tissue, and therefore inhibit movement of electrode positioning member in direction 253. In the preferred embodiment, the second tines may be omitted from electrode attachment member 224a. As will be described in greater detail below, electrode attachment member 224a passes through tissue twice. Therefore, second tines, which generally remain at the entrance side of the tissue as described above, would inhibit the passage of electrode attachment member 224a entirely though the tissue or may cause tearing or other injury to the tissue. Consequently, second tines may be omitted from electrode attachment member 224a. If it desired to provide additional anchoring to the tissue, an anchor sleeve 251 may be provided. Anchor sleeve preferably is a frusto-conical portion attached to electrode attachment member 224a at its smaller end portion. It extends radially outward from electrode attachment member 224a may be typically oriented at an acute angle with respect to the direction of travel 252. In this orientation, anchor sleeve 251 provides resistance to movement of electrode attachment member 224a in direction 252. Anchor sleeve 251 is preferably resilient. Anchor sleeve 251 has the ability to flip "inside-out" towards parallelism with the electrode attachment member 224a in response to a predetermined contact force of the electrode attachment member with the tissue 5, allowing relative movement of the electrode attachment member 224a in direction 252 through tissue, and to subsequently resiliently return to the position illustrated in FIG. 14.

As described above with respect to conductors 52/54/56/58, each of the electrodes A 226, B 228, C 230, and D 232 are respectively electrically connected to a distinct conductor 252/254/256/258, each of which is connected electrically to the pulse generator 212 at the proximal end. Alternatively, the electrodes may be connected via two conductors to the generator 212, to create a permanent quadrapole.

Installation of the Alternative Embodiment

The stimulator 200 is installed substantially as described above with respect to FIGS. 3–5 in a simple, minimally-invasive installation procedure. According to an early stage of the invention, the approximate location of the gastrointestinal tissue is located by the physician. An incision is made in the patient in the surface of the skin above the operative site. A series of trocars may be installed through the patient's skin which allow access for surgical instrumentation while maintaining insufflation pressure. The electrode assembly 216 may be contained within a sleeve that is passed through a trocar. It is contemplated that the sleeve may be omitted when electrode assembly is passed through the trocar or other access opening. After trocar passage, the electrode assembly may be freed from the sleeve by mechanical means.

A stage of attachment of the electrode 216 assembly to the tissue follows. The attachment may be achieved in several ways. As illustrated in FIG. 15, the penetration mechanism 238 passes through the tissue S. More particularly, distal cutting end portion 242 pierces the tissue S at the outer surface N at entrance site V and is advanced as indicated by the arrow. First tines 248a, as described above, are angled to facilitate passage as shown into the tissue. Tines 248a are preferably resilient and may deflect towards parallelism with the electrode attachment member 22/1a during insertion. Preferably, forceps, such as endoscopic forceps, may be used by the physician to advance the electrode attachment member 224a into the tissue.

As electrode attachment member 224a is further advanced through tissue S, anchor sleeve 251 abuts the tissue at entrance side V. (The initial configuration of anchor sleeve 251 is illustrated in dashed line.) Upon further advancement of sleeve 251 into tissue S with increased contact force applied by the physician, anchor sleeve 251 resiliently flips into a backwardly oriented configuration towards parallelism with electrode attachment member 22/1a as indicated by the pair of curved arrows (this backward configuration is illustrated in solid line in FIG. 15).

While in this backward facing configuration, electrode attachment member 22/1a may be advanced through the tissue such that electrode attachment member 22/1a exits the surface N of the tissue S at exit site U. Further advancement allows bridging portion 225 to exit the tissue S at exit site U. First tines 248b pass through the tissue S until electrodes C 230 and D 232 are positioned in tissue S, as illustrated in FIGS. 16(a) and 16(b). Penetrating mechanism 238 is positioned such that cutting end portion 242 may pierce the tissue at the surface N at entrance site Y. Advancement of electrode positioning member 22/1a allows first tines 248a to pass through the tissue S until electrodes A 226 and B 228 are positioned in tissue S, and penetration mechanism 238 and first tines 248a pass through the tissue S at exit site Z. Anchor sleeve 251 returns to its forward facing configuration to anchor electrode attachment member 22/1a between first tines 248a and anchor sleeve 251. Penetration mechanism 238 may be removed from electrode assembly 216 by severing connecting member 244, as described above with respect to FIG. 4.

Second Alternative Embodiment

Figure 17:
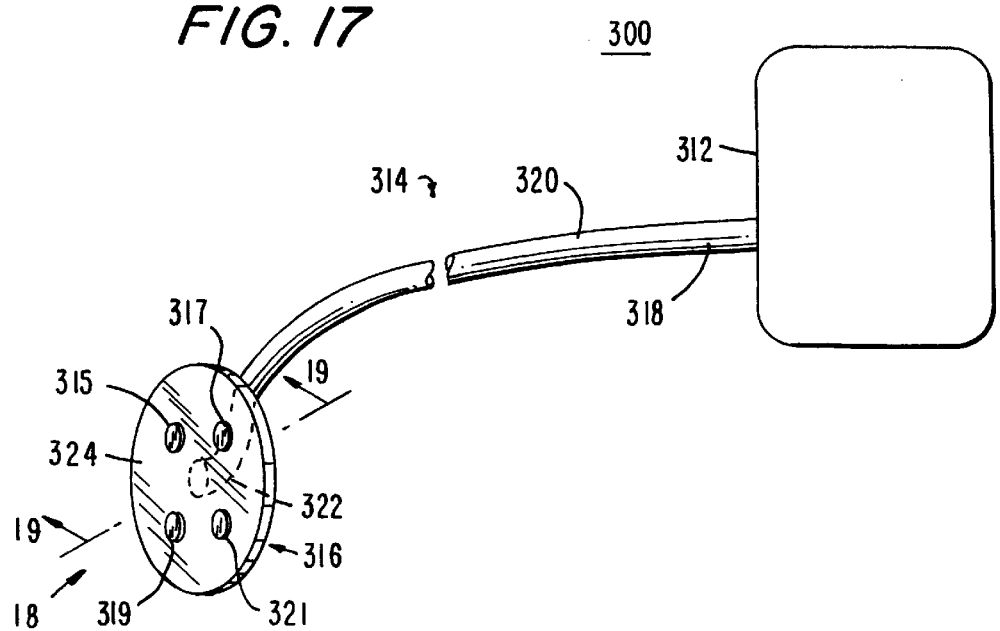
FIG. 17 is a simplified perspective view of a preferred embodiment in accordance with the invention.

Another alternative embodiment of a neuromuscular stimulator is illustrated in FIG. 17, and designated generally with reference number 300. The stimulator apparatus and method of installation are substantially described in Jenkins U.S. patent application Ser. No. 09/466,532, filed Dec. 17, 1999, which is incorporated by reference in its entirety herein. The stimulator 300 includes an implantable pulse generator 312, a lead system 314 and an electrode assembly 316. The implantable pulse generator 312 provides a series of electrical pulses to the neuromuscular tissue of the viscera. The electrical stimulation lead 314 includes a proximal connector end 318 to interface with the implantable pulse generator 312, a medial lead body portion 320, and a distal end 322, for electrical connection with the electrode assembly 316.

Four electrodes, i.e., "electrode A" 315, "electrode B" 317, "electrode C" 319, and "electrode D" 321 are installed in contact with the surface of the stomach tissue, or other viscera. In a preferred embodiment, the electrodes A 315, B 317, C 319, and D 321 are supported by an electrode attachment member 324, which may be attached to the stomach by sutures or staples. As will be described in greater detail below, the electrodes A 315, B 317, C 319, and D 321 and electrode attachment member, or patch 324 may be inserted to the body cavity laparoscopically through a trocar or other minimally invasive surgical access opening to fit through the restrictive diameter of the trocar, patch 324 is preferably made from a flexible material so it can be folded during passage through the trocar.

Figure 19:
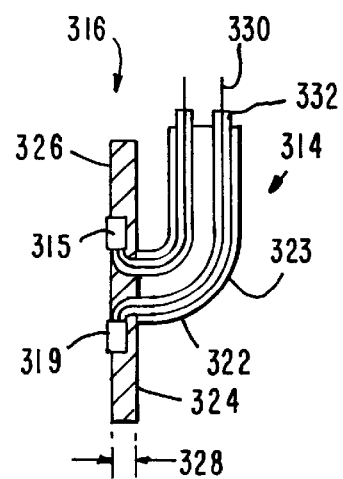
FIG. 19 is a simplified sectional view taken from line 19—19 of FIG. 17 of a component of the apparatus in accordance with the invention.
Figure 18:
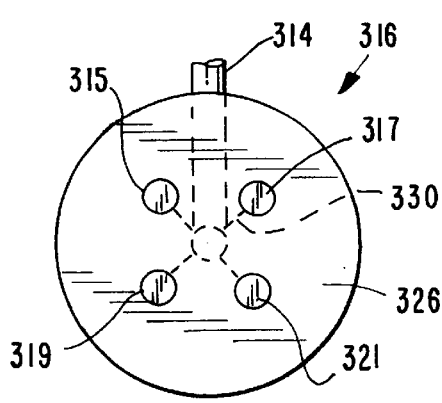
FIG. 18 is an elevational view taken from direction 18 of FIG. 17 of a component of the apparatus in accordance with the invention.

As illustrated in FIGS. 18 and 19, the stimulation electrodes A 315, B 317, C 319, and D 321 and the electrode attachment member, such as patch 324, are adjacent the distal end portion 322 of the lead 314. The stimulation electrodes may be fabricated from a metallic or other conductive material, attached to or partially embedded within the patch 324. The electrodes are exposed at the distal surface 326 of the patch 324, which may be attached to the surface of the tissue being stimulated.

The patch is provided with substantially flat distal surface 326, which will generally refer to the configuration of the surface as relatively broad in relation to the thickness 328 or depth of the patch 324 as a whole. In a preferred embodiment, patch 324 has a diameter of, for example, about 1 to 3 cm and a thickness of, for example, about 3 to 5 mm. The distal surface 326 may be, e.g., substantially planar, curved (e.g., convex, concave, or another appropriate curvature). Alternatively, the distal surface 326 may be flexible to conform to the surface of the tissue to which it is to be attached, etc. The electrodes A 315, B 317, C 319, and D 321 are supported by the patch 324, and positioned adjacent the distal surface 326 in order to provide an electrical interface between the electrodes A 315, B 317, C 319, and D 321 and the surface of the tissue being stimulated. The interface, e.g., the interface surface area, between the electrodes and the tissue being stimulated is sufficient to allow for the use of a low impedance stimulation. Each electrode may be of a shape suitable for providing this surface area.

The patch 324 may be constructed from a flexible material, such as, e.g., silicone elastomer or similar material. The base materials for the electrode 16 may include, e.g., platinum, platinum-iridium alloys, titanium, and the like. The electrodes A 315, B 317, C 319, and D 321 may be in an uncoated state or may be coated with materials such as iridium oxide or titanium nitride, or the electrodes may be platinized or carbonized. In a preferred embodiment, the patch has a substantially circular configuration. It is understood that patch 324 may be fabricated in any suitable configuration, such as, for example, oval, square, rectangular, etc. The electrodes 315/317/319/321 may be distributed around the distal surface 326 substantially equidistantly from the center of the distal surface 326. For example, if an array of electrodes is being used for multiple stimulation vectors, and eccentric placement of the electrodes may be preferred to phase the stimulating pulses, and consequently the contractions. The arrangement of the patch 324 supporting electrodes A 315, B 317, C 319, and D 321 provides an advantage to the physician in that the orientation of the electrodes with respect to one another, i.e., equidistant, is fixed prior to installation. Therefore, the physician is spared the task of installing individual electrodes, thereby reducing the time required for electrode installation.

With continued reference to FIG. 19, the implantable electrical stimulation lead 314 includes a plurality of distinct conductors 330, each of which is connected electrically to a corresponding electrode or electrodes A 315, B 317, C 319, and D 321 on the distal end. Alternatively, two conductors may be provided in the lead. This configuration may be used to connect the four electrodes to provide a permanent quadrapole, for example, as illustrated in FIG. 7b. The conductors may be surrounded by an electrically insulative material 332 to isolate the non-common conductors from each other, as necessary, and to isolate the conductor 330 from the physiological environment. In a preferred embodiment, the portion 322 may be configured with an angled portion 323, wherein the lead may be initially oriented perpendicular to the distal surface 326 of electrode attachment member 324 and subsequently be oriented substantially parallel to the surface 326. This configuration facilitates laparoscopic installation, as described above. The lead body 320 may include a plurality of conductive coils (not shown) isolated within an electrically insulative material such as silicone elastomer. The lead body 320 may utilize a coaxial or parallel conductor design. The conductive coils of the lead body shall electrically connect the proximal terminations of the lead to their corresponding distal electrode or electrodes 316.

With continued reference to FIG. 18, the patch 324 is constructed to allow attachment to the surface of the tissue being stimulated. In a preferred embodiment, the patch material is selected to allow sutures or staples to pass directly therethrough to permit the attachment to the tissue. Alternatively, it is contemplated that the patch may be provided with a plurality of pre-formed openings or apertures (not shown) to permit the passage therethrough of sutures or staples.

According to the preferred embodiment, the patch is flexible. The flexibility of the patch permits the patch to be reduced to a compact form by rolling or folding. The patch 324 may be inserted in a compact form into a patch holder, such as an introduction sleeve.

Installation of the Second Alternative Embodiment

The above-described configuration of the electrodes and electrode attachment member provides for a simple, minimally-invasive installation procedure in accordance with the invention. According to an early stage of the invention, the approximate location of the gastrointestinal tissue is located by the physician. An incision is made in the patient in the surface of the skin above the operative site. According to a preferred embodiment, an obturator device may be used to provide the incision and install a trocar. The process of insufflation may be used, wherein an inert gas such as carbon dioxide is introduced under pressure, to enlarge the body cavity and provide improved visualization and access within the body cavity. A series of trocars may be installed through the patient's skin which allow access for surgical instrumentation while maintaining insufflation pressure. A laparoscope or similar remote viewing apparatus may be inserted through one of the trocars in order to allow viewing of the process of attachment of the electrode attachment member to the surface of the tissue, such as the stomach tissue 5, in this example.

The electrode attachment member, e.g., patch 324 is provided in compact form in the introduction sleeve. In the case of the electrodes positioned on the elongated electrode attachment member 224, the patch could be contained to a width of 1 cm or less. The distal patch 324 within a sleeve is passed through a trocar. It is contemplated that the sleeve may be omitted when patch 324 is passed through the trocar or other access opening.

After trocar passage, the patch 324 may be freed from the sleeve by mechanical means. For example, mechanical grasping apparatus, such as a grasper, may be used to hold the patch with grasping jaws to remove the patch 324 from an end portion of the sleeve.

Figure 20:
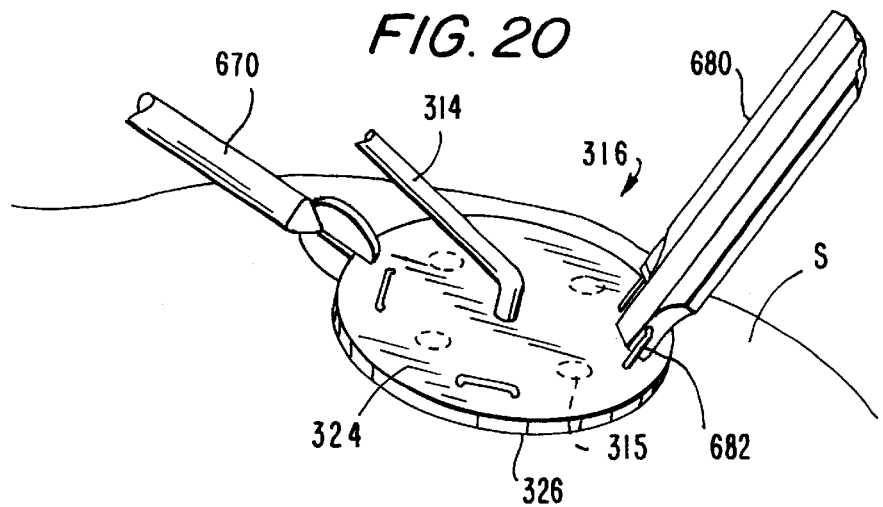
FIG. 20 is a simplified view illustrating a stage in the process of installing the apparatus of FIG. 17 in accordance with the invention.

The patch 24 is returned to its open, uncompacted form, as illustrated in FIG. 20. The grasper 670 may be used to position the patch 324 adjacent the surface of the viscera S of the stomach. More particularly, the distal surface 326 of the patch 324 is placed adjacent the tissue such that the exposed portions of the electrodes A 315, B 317, C 319, and D 321 are near the surface of the viscera in order to provide an electrical interface between the electrodes and the surface of the gastrointestinal tissue. The interface is sufficient to allow for a low impedance stimulation. Typical impedances may range from about 300 to 800 ohms, with stimulating voltages in the range of 2.5 to 5.0 volts and stimulating currents in the range of about 4 to 6 milliamps. The voltages and currents are dependent upon the stimulating pulse widths and frequency.

Figure 21:
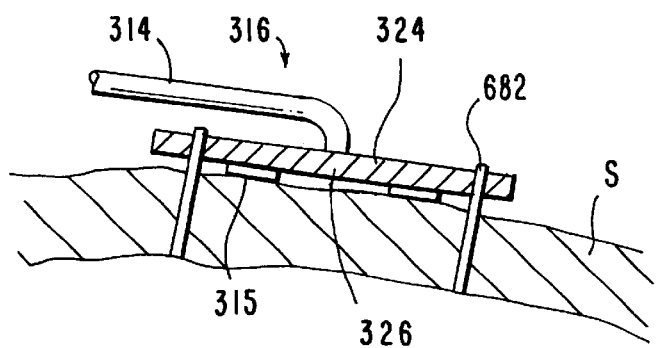
FIG. 21 is a sectional view illustrating the apparatus installed in accordance with the invention.

Attachment of the patch to the viscera may be achieved in several ways. As illustrated in FIG. 20, a stapling apparatus, such as endoscopic stapler or suture applying apparatus 680, may be used. Stapler 680, as is known in the art, may be sized and configured for insertion through the trocar or other minimally invasive surgical access opening, and remotely actuable by the physician. The stapler 680 applies at least one or more staples or sutures 682 to attach the patch to the viscera. The installed patch 324 is illustrated in FIG. 21. Distal surface 326 is illustrated in a substantially planar configuration. However, because patch 324 may be flexible, the distal surface 326 may curve to conform to the surface of the viscera S.

Figure 22:
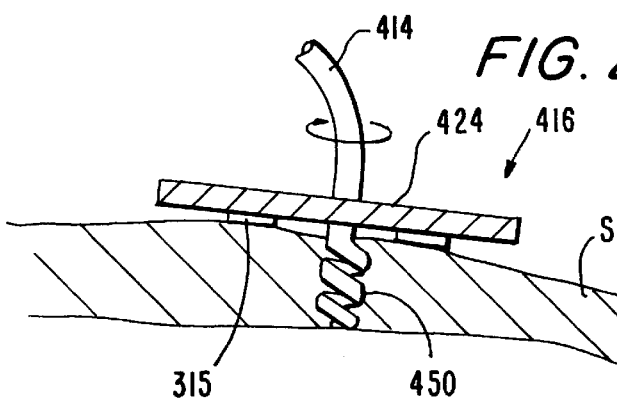
FIG. 22 is a view similar to FIG. 21, illustrating an alternative embodiment in accordance with the invention.

FIG. 22 illustrates an alternative embodiment of the apparatus in accordance with the invention. Electrode assembly 416 is substantially identical to electrode attachment member 316 described above with respect to FIGS. 17–20, with the differences noted herein. In particular, electrode assembly 416 is provided with a corkscrew-type attachment member 450. The corkscrew 450 may be easily applied to the tissue by rotating the electrode assembly 416 with respect to the tissue. According to this embodiment, the angled portion, referred to as angled portion 323 of apparatus 300, may be omitted from lead 414 in order to facilitate the rotational mounting of electrode assembly 416. Alternatively, the corkscrew attachment member may be used to directly pierce the tissue S with rotation, such that the concentric rings of the corkscrew attachment member 450 provide sufficient anchoring against removal of the electrode assembly 416 from the tissue S.

Alternate Adaption Defeating Embodiment

With reference to FIG. 23, another alternative embodiment of a neuromuscular stimulator utilizes the described real-time clock and calendar functionality to assist in defeating the body's natural tendency for adaption. Although, at first an electrical stimulation may produce very good results, over time the body "adapts" so that therapeutic results are no longer achieved. By changing the electrical stimulation parameters on a periodic basis, the body's stimulation input is constantly changing, and hence, the body cannot adapt. Therefore, it would be desirable if the implantable stimulator could make this change automatically, so that the patient does not have to visit the doctor. While the patient could have a patient programmer, to make parameter changes on a periodic basis, this would be less desirable, as there would be no record of the patient input, compliance could be poor (the patient may not program any changes), or the patient could put in parameters which are not therapeutic. Thus, the above-described calendar and time clock capabilities make possible systems and methods implementing an automatic change in stimulation parameters on a periodic basis. As a further enhancement to automatic selectable algorithms for defeating adaption, devices and methods should allow for two or more sets of electrodes that could be attached at different locations on the neuromuscular tissue of the viscera of the organ structure, including the gastrointestinal tract.

For example, one of a plurality of electrode sets could be on and one off, for the duration of, e.g., one month, and then this could be switched for another month, and, in a third month, maybe both could be on at the same time. The switching of on-off between electrodes, or sets of electrodes, can be triggered by the time clock. In addition, a real-time clock allowing a trigger for on and off modes, the time clock could also allow for a trigger to change parameters. Such parameters that could be changed are pulse width, amplitude, duty cycle (amount of time of pulse and time between pulses, or series of pulses), frequency, polarity, choice of unipolar versus bi-polar, and electrode on-off.

The IGS stimulator 400 of FIG. 23 is substantially similar to stimulator 10 with the differences noted herein, and includes an implantable pulse generator 412, a lead system 414, and an electrode assembly 416. The electrical stimulation lead 414 includes a proximal connector end 418 to interface with the implantable pulse generator 412, a medial lead body portion 420, and a distal end portion 422, for electrical connection with the electrode assembly 416.

According to the alternative embodiment, the electrode assembly 416 includes a plurality or a multiplicity of pairs of substantially identical electrode attachment members 424a, 424b, 424c, and 424d arranged in a series configuration positioned at various different locations along the neuromuscular tissue of the viscera of the organ structure, including the gastrointestinal tract. A bridging portion 425 may connect electrode attachment member 424a with electrode attachment member 424b. The electrode assembly 416 includes a single penetration mechanism 438 to pass through the tissue in which the electrodes A 426, B 427, C 428, D 429, E 430, F 431, G 432, H 433 are desired to be implanted. Penetration mechanism 438 is connected to the electrode attachment member 424a by a connecting member 444.

The penetration mechanism 438 may include a curved portion 440 and a distal cutting end portion 442. Electrodes A 426 and B 427, electrodes C 428 and D 429, electrodes E 430 and F 431, and electrodes G 432 and H 433 may be anchored with respect to the patient's tissue by securing members 446. Securing members 446 substantially similar to securing members 46 may consist of first tines 448a/448b/448c/448d and second tines 450a/450b. The first tines 448a/448b/448c/448d may be leading tines, that is, tines 448a/448b/448c/448d define an obtuse angle with respect to the direction of travel 452 and 453, respectively. This configuration aids in the passage of electrode attachment members 424a/424b/424c/424d in the direction 452 and electrode attachment members 424a/424b/424c/424d in the direction 453, while inhibiting movement in the opposite direction. Second tines 450b may define an acute angle with direction 453. In operation, second tines 450b do not penetrate the thickness of the tissue to be stimulated, but may provide contact with the entrance site of the tissue, and therefore inhibit movement of electrode positioning member in direction 453. If it desired to provide additional anchoring to the tissue, an anchor sleeve 451 may be provided.

The electrodes 426–433 are separated over a sufficient length such that they can be connected at different locations, positioned along the curvature of a human stomach. Thus the electrodes 426–433 can be implanted on different organs which require peristaltic flow of material, e.g., stomach, colon, intestines, bowels, etc., from which the pacemaker can control different electrodes implanted on different organs. In the configurations contemplated, the use of plural or multiple electrodes positioned at multiple sites either on the same organ or on different organs facilitates the enhanced performance discussed herein. The responses of different patients to different electrical stimuli may be adjusted. The response of an organ in the gastrointestinal tract to different electrical stimulations at different regions of an organ may also be monitored such that the appropriate program algorithm may be implemented in software for use with the pacemaker for stimulation in independent non-phased modes of operation for maintaining therapeutic regulation while defeating the body's natural tendency for adaption.

By using a crystal controlled oscillator (which may be either internal component of the information processor (CPU 44) or a separate component), accuracy is achieved by a real-time clock counter 46. Typically, a 32 to 100 kilohertz crystal clock may be used to provide timing. Stimulation pulse width is typically 100 to 500 microseconds (10 to 50 oscillations of 100 kilohertz clock), and the pulse interval may be, e.g., 25 milliseconds or 2500 clock oscillations. It is useful to synchronize time inside the processor. The variations in pulsing algorithms allow the eight electrodes, e.g., electrodes A 426, B 427, C 428, D 429, E 430, F 431, G 432, H 433, to stimulate the tissue individually, and in any combination. The ability to vary the stimulation applied to tissue, such as that of the stomach, is important to entrain the tissue. The characteristic of the stomach tissue addressed herein is that such neuromuscular tissue may become adapted to constant stimulation due to the body's natural tendency toward adaption. Thus the ability to change the location, direction, and intensity of stimulation may prevent adaption. Consequently, the waveform may be programmed to apply differing waveforms and/or at differing locations during each particular week in the treatment period. The real time clock may also supply data corresponding to the day of the week during the treatment period. Alternatively, the real time clock may supply data corresponding to a month of the year during the treatment period, such that the waveform may vary from month-to-month as the treatment progresses. Moreover, the real time clock may also supply data corresponding to the day of the month, and/or the day of the year.

The electrode switching circuitry and the software algorithms establish the function of each electrode and the polarity of the electrode. The switching circuitry is controlled by the microprocessor CPU 44 and is programmable. In the preferred embodiment, the electrode switching circuitry will enable a pair of electrodes to be used for sensing, and a pair or pairs of electrodes to be used for stimulation. The stimulation and sensing may utilize the same electrodes. During the stimulation period, the electrode switching circuitry can change the polarity of the stimulation electrodes to create multi-phasic pulses, alternating polarity between pulses or a series of pulses, and different stimulation vectors. Likewise, the switching circuitry can enable different pairs of sensing electrodes to sample gastric electrical activity at various sensing locations or along different vectors. Complex sensing patterns can be invoked to differentiate slow wave propagation direction and intervals. Complex switching schemes and various pulsing algorithms can be stored in memory and be activated as a program. The switching software would be designed to ensure that each configuration would have at least one bipolar pair to complete the electrical circuit.

The memory is used to store information and programs for the IGS stimulator 400. The memory receives the sensed information about the intrinsic gastric activity from the microprocessor, analyzes that information to determine if the activity is normal according to a selected algorithm(s), and provides that analysis output to the microprocessor to initiate the therapy in accordance with the particular programming selected. Multiple programs may be stored in memory to establish specific profiles of IGS stimulator 400 activation, response, and performance. The memory may also be used to store various parameters that indicate device performance, gastric activities, and therapies administered.

The foregoing is merely illustrative of the principles of this invention and various modifications can be made by those skilled in the art without departing from the scope and spirit of the invention.

What is claimed is:

1. Method of applying electrical stimulation to the neuromuscular tissue in the viscera, comprising:

providing an electrode attachment assembly supporting a plurality of electrode pairs thereon for attachment to the tissue such that the plurality of electrode pairs are positionable at substantially different locations thereon;

laparoscopically inserting the electrode attachment assembly through a surgical access opening in the patient;

attaching the electrode attachment assembly to the neuromuscular tissue such that the plurality of electrode pairs are spaced apart, thereby forming an electrical interface between each of the plurality of electrode pairs and the neuromuscular tissue; and electrically stimulating the tissue in a time-varying manner with selectable individual pairs of the plurality of electrode pairs with a pulse generator.

2. Method defined in claim 1, wherein the providing an electrode attachment assembly comprises providing a first electrode attachment member configured to pass through the tissue and supporting a first electrode pair thereon and a second electrode attachment member configured to pass through the tissue and supporting a second electrode pair thereon spaced a first distance apart, and a flexible bridging portion attached to the first and second electrode attachment members and configured to allow relative positioning of the first and second electrode attachment members at differing positions on the neuromuscular tissue of the viscera of the organ structure, including the gastrointestinal tract.

3. Method defined in claim 2, wherein the plurality of electrode pairs comprise a first and a second diagonally-oriented electrode pair, and wherein electrically stimulating the tissue comprises:

applying electrical stimulation across the first diagonally-oriented electrode pair during a first time period; and independently applying electrical stimulation across the second diagonally-oriented electrode pair during a second time period.

4. Method defined in claim 3, further comprising:

applying electrical stimulation across the first diagonally-oriented electrode pair during a third time period such that the polarity of each of the electrodes comprising the first diagonally-oriented electrode pair is reversed from the polarity of the respective electrodes during the first time period; and independently applying electrical stimulation across the second diagonally-oriented electrode pair during a fourth time period such that the polarity of each of the electrodes comprising the second diagonally-oriented electrode pair is reversed from the polarity of the respective electrodes during the second time period.

5. Method defined in claim 2, wherein the plurality of electrode pairs comprise a first, second, third and fourth adjacent electrode pairs, and wherein electrically stimulating the tissue comprises:

applying electrical stimulation across the first adjacent electrode pair during a first time period;

applying electrical stimulation across the second adjacent electrode pair during a second time period;

applying electrical stimulation across the third adjacent electrode pair during a third time period; and applying electrical stimulation across the fourth adjacent electrode pair during a fourth time period, said first, second, third, and fourth time periods being triggered in an independent non-phased relationship to one another.

6. Method defined in claim 1, wherein the providing an electrode attachment assembly comprises providing an electrode attachment member supporting the plurality of electrode pairs on a distal surface thereon spaced substantially equidistantly apart; and wherein the attaching the electrode attachment member to the neuromuscular tissue comprises attaching the distal surface of the electrode attachment member to the surface of the viscera, thereby forming an electrical interface between each of the first, second, third, and fourth electrodes and the neuromuscular tissue.

7. Apparatus for electrically stimulating neuromuscular tissue of the viscera of the organ structure, including the gastrointestinal tract by applying electrical pulses to the neuromuscular tissue, the electrical pulses supplied by a pulse generator, comprising:

first and second electrodes electrically connected with the pulse generator;

first electrode-pair attachment member having a body portion configured to penetrate through the tissue and supporting the first and second electrodes thereon spaced a first distance apart;

third and fourth electrodes electrically connected with the pulse generator;

second electrode-pair attachment member having a body portion configured to penetrate through the tissue and supporting the third and fourth electrodes thereon spaced a second distance apart;

bridging portion attached to the first and second electrode-pair attachment members and configured to allow relative positioning of the first and second electrode-pair attachment members in the tissue such that the first, second, third and fourth electrodes may be substantially equidistantly spaced apart; and a pulse generator configured to supply electrical pulses to the first, second, third, and fourth electrodes in a time-varying manner with selectable pairs of the electrodes in an independent non-phased relationship to one another.

8. Apparatus defined in claim 7, wherein the pulse generator comprises a switching matrix responsive to a controller for applying the selectable pairs of electrodes with stimulating pulses of predetermined polarities.

9. Apparatus defined in claim 7, wherein the pulse generator is configured to apply electrical stimulation between the first diagonally-oriented electrode pair having a first polarity and the second diagonally-oriented electrode pair simultaneously having a second polarity.

10. Apparatus defined in claim 7, wherein the first, second, third, and fourth electrodes comprise a first and a second diagonally-oriented electrode pair, and wherein the pulse generator is configured to apply electrical stimulation across the first diagonally-oriented electrode pair during a first time period, and apply electrical stimulation across the second diagonally-oriented electrode pair during a second time period.

11. Apparatus defined in claim 10, wherein the pulse generator is further configured to apply electrical stimulation across the first diagonally-oriented electrode pair during a third time period such that the polarity of each of the electrodes comprising the first diagonally-oriented electrode pair is reversed from the polarity of the respective electrodes during the first time period, and apply electrical stimulation across the second diagonally-oriented electrode pair during a fourth time period such that the polarity of each of the electrodes comprising the second diagonally-oriented electrode pair is reversed from the polarity of the respective electrodes during the second time period.

12. Apparatus defined in claim 7, wherein the first, second, third, and fourth electrodes comprise a first, second, third and fourth adjacent electrode pair, and wherein the pulse generator is configured to apply electrical stimulation across the first adjacent electrode pair during a first time period, apply electrical stimulation across the second adjacent electrode pair during a second time period, apply electrical stimulation across the third adjacent electrode pair during a third time period, and apply electrical stimulation across the fourth adjacent electrode pair during a fourth time period.

13. A method for electrically stimulating neuromuscular tissue of the viscera of the organ structure, including the gastrointestinal tract, comprising:

connecting a plurality of electrodes to at least one organ in the gastrointestinal tract of a patient along a peristaltic flow path, each of said plurality of electrodes being connected at a different location along said peristaltic flow path;

providing electrical pulses to said organ from a first set of said plurality of electrodes; and providing second electrical pulses to said organ from a second set of said plurality of electrodes, said electrical pulses provided by said plurality of electrodes being in an independent non-phased relationship for maintaining therapeutic regulation of peristaltic flow through said at least one organ in said gastrointestinal tract while defeating the body's natural tendency for adaption.

14. The method of claim 13 comprising providing the first electrical pulses and the second electrical pulses according to a real-time clock function.

15. The method of claim 13 further comprising the step of independently regulating a pulse amplitude, a pulse timing, and a pulse duration for said electrical pulses for each one of said plurality of electrodes.

16. A gastric pacemaker for controlling the peristaltic pace of digestive organs by electrically stimulating neuromuscular tissue of the viscera of the organ structure, including the gastrointestinal tract, comprising:

a plurality of stimulation electrodes sequentially positionable on at least one digestive organ along a peristaltic flow path;

controller for controlling electrical pulse parameters for a first set of said plurality of stimulation electrodes;

said controller controlling electrical pulse parameters for a second set of said plurality of stimulation electrodes in an independent non-phased relationship according to a desired peristaltic flow; and circuitry for providing electrical pulses to each of the first set and the second set of said plurality of stimulation electrodes in accordance with a real-time clock function.

17. A gastric pacemaker as recited in claim 16 further comprising a sensor electrode connectable to said digestive organ for sensing a response of said organ to an electrical pulse stimulation.

18. A gastric pacemaker as recited in claim 16, wherein at least one of said plurality of stimulation electrodes also functions as a sensing electrode for sensing a response of said organ to an electrical pulse.

19. A method for electrically stimulating neuromuscular tissue of the viscera of the organ structure, including the gastrointestinal tract, comprising:

connecting a plurality of electrodes to at least one organ in the gastrointestinal tract of a patient along a peristaltic flow path, each of said plurality of electrodes being connected at a different location along said peristaltic flow path;

providing electrical pulses to said organ from a first set of said plurality of electrodes; and providing second electrical pulses to said organ from a second set of said plurality of electrodes for maintaining therapeutic regulation of peristaltic flow through said at least one organ in said gastrointestinal tract while defeating the body's natural tendency for adaption.

20. The method of claim 19, further comprising the step of providing said first and second electrical pulses according to a real-time clock function.

21. The method of claim 20, further comprising the step of providing time-of-day and date information from said real-time clock function to a programmable calendar.

22. The method of claim 21, wherein said electrical pulses maybe varied in accordance with said real-time clock function for enabling a stimulating waveform from said electrical pulses to vary over periods of time based on a setting of said real-time clock function.

23. The method of claim 21, wherein said real-time clock functions serve as a trigger for changing stimulation parameters on a periodic basis.

24. The method of claim 23, wherein said real-time clock functions serve as a trigger for changing stimulation parameters on a periodic basis.

25. The method of claim 24, wherein said stimulation parameter comprises a pulse width of said electrical pulses.

26. The method of claim 24, wherein said stimulation parameter comprises an amplitude of said electrical pulses.

27. The method of claim 24, wherein said stimulation parameter comprises a duty cycle of said electrical pulses.

28. The method of claim 24, wherein said stimulation parameter comprises a frequency of said electrical pulses.

29. The method of claim 24, wherein said stimulation parameter comprises a polarity of said electrical pulses.

30. The method of claim 24, wherein said stimulation parameter comprises activating and deactivating generation of said electrical pulses for a predetermined length of time.

31. The method of claim 20, wherein said electrical pulses provided by said plurality of electrodes are in an independent non-phased relationship.

* * * * *